(12) United States Patent
Falcioni et al.

(10) Patent No.: US 6,983,233 B1
(45) Date of Patent: Jan. 3, 2006

(54) COMBINATORIAL PARAMETER SPACE EXPERIMENT DESIGN

(75) Inventors: Marco Falcioni, San Francisco, CA (US); C. Eric Ramberg, Sunnyvale, CA (US); Youqi Wang, Atherton, CA (US)

(73) Assignee: Symyx Technologies, Inc., Santa Clara, CA (US)

(*) Notice: Subject to any disclaimer, the term of this patent is extended or adjusted under 35 U.S.C. 154(b) by 447 days.

(21) Appl. No.: 09/840,003

(22) Filed: Apr. 19, 2001

Related U.S. Application Data

(60) Provisional application No. 60/198,208, filed on Apr. 19, 2000.

(51) Int. Cl.
*G06F 17/50* (2006.01)
*G06G 7/48* (2006.01)

(52) U.S. Cl. .............. 703/12; 703/6; 703/17; 703/22; 702/19; 702/20

(58) Field of Classification Search .......... 703/6, 703/11, 12, 13, 17, 22; 702/19, 20

See application file for complete search history.

(56) References Cited

U.S. PATENT DOCUMENTS

| | | |
|---|---|---|
| 5,143,854 A | 9/1992 | Pirrung et al. |
| 5,324,483 A | 6/1994 | Cody et al. ................. 422/131 |
| 5,331,573 A | 7/1994 | Balaji et al. ................. 364/500 |
| 5,356,756 A | 10/1994 | Cavicchi et al. ............ 430/315 |
| 5,386,507 A | 1/1995 | Teig et al. ................... 395/161 |
| 5,434,796 A | 7/1995 | Weininger ................... 364/496 |
| 5,526,281 A | 6/1996 | Chapman et al. ........... 364/496 |
| 5,571,639 A | 11/1996 | Hubbell et al. |
| 5,714,127 A | 2/1998 | DeWitt et al. ............... 422/131 |
| 5,759,779 A | 6/1998 | Dehlinger ................... 435/436 |
| 5,763,263 A | 6/1998 | Dehlinger ................... 435/287 |
| 5,854,992 A | 12/1998 | Shakhnovich et al. ........ 702/27 |
| 5,862,514 A | 1/1999 | Huse et al. .................... 702/22 |
| 5,914,891 A | 6/1999 | McAdams et al. ........... 364/578 |
| 5,930,154 A | 7/1999 | Thalhammer-Reyero .... 364/578 |
| 5,959,297 A | 9/1999 | Weinberg et al. ........... 250/288 |
| 5,980,096 A | 11/1999 | Thalhammer-Reyero .... 364/578 |
| 6,004,617 A | 12/1999 | Schultz et al. ................. 427/8 |
| 6,030,917 A | 2/2000 | Weinberg et al. ........... 502/104 |
| 6,034,775 A | 3/2000 | McFarland et al. ......... 356/364 |
| 6,044,212 A | 3/2000 | Flavin et al. .......... 395/500.27 |
| 6,045,671 A | 4/2000 | Wu et al. ............... 204/298.11 |
| 6,081,766 A | 6/2000 | Chapman et al. ............. 702/27 |
| 6,144,897 A | 11/2000 | Selliers ...................... 700/269 |
| 6,175,816 B1 | 1/2001 | Flavin et al. .................. 703/13 |
| 6,187,164 B1 | 2/2001 | Warren et al. ................. 205/81 |
| 6,188,965 B1 | 2/2001 | Mayo et al. ................... 702/27 |
| 6,507,945 B1 | 1/2003 | Rust et al. ................... 717/103 |
| 6,640,191 B1 | 10/2003 | Deem et al. ................... 702/19 |
| 2002/0152057 A1 | 10/2002 | Wang et al. ..................... 703/6 |

FOREIGN PATENT DOCUMENTS

| | | |
|---|---|---|
| EP | 0 796 654 | 9/1997 |
| WO | WO 96/11878 | 4/1996 |
| WO | WO 99/59722 | 11/1999 |
| WO | WO 00/23921 | 4/2000 |
| WO | WO 02/04112 | 1/2002 |

OTHER PUBLICATIONS

H.–D. Klein, "Statistische Versuchsplanung", 1995, Nachr. Chem. Tech. Lab. vol. 43, pp. 1078, 1080–1082 (with English translation).

X.D. Xiang et al., "A Combinatorial Approach to Materials Discovery", Jun. 23, 1995, Science, vol. 268, pp. 1738–1740.

Linda C. Hsieh–Wilson, et al., "Lessons from the Immune System: From Catalysis to Materials Science", © 1996 American Chemical Society, vol. 29, pp. 164–170.

J.J. Hanak, "The "Multiple–Sample Concept" in Materials Research: Synthesis, Compositional Analysis and Testing of Entire Multicomponent Systems", © 1970 Chapman and Hall Ltd., pp. 964–971.

Eric W. McFarland and W. Henry Weinberg, "Approaches for Rapid Materials Discovery Using Combinatorial Methods", 1998, Mat. Tech. vol. 13.3, pp. 107–120.

Earl Danielson, et al., "A combinatorial approach to the discovery and optimization of luminescent materials", Oct. 30, 1997, Nature, vol. 389, No. 30, pp. 944–948.

Xiao–Dong Sun, "Solution–Phase Synthesis of Luminescent Materials Libraries", 1997, Advanced Materials, vol. 9, pp. 1046–1049.

Peter G. Schultz and Xiao–Dong Xiang, "Combinatorial approaches to materials science", 1998, © Current Chemistry ISSN 1359–0286, pp. 153–158.

Statistica vol. IV: Industrial Statistics, Copyright © StatSoft, 1995, pp. 4177–4473.

MODDE 4.0, "Graphical Software for Design of Experiments", ©1992–1997 Umetri AB, pp. 1–1 to 14–2.

X.–D. Xiang and P.G. Shultz, "*The Combinatorial Synthesis and Evaluation of Functional Materials*", 1997, Physica C., vol. 282, pp. 428–430.

S. P.A. Foder, J. Leighton Red, M. C. Pirrung, L. Stryer, A. T. Lu, D. Solas, "Light–directed, spatially addressable parallel chemical synthesis", Science, (1991) vol. 251, pp. 767–773.

(Continued)

Primary Examiner—Marianne P. Allen

(57) ABSTRACT

Methods and apparatus, including computer program apparatus, implementing techniques for designing sets of combinatorial experiments. A set of experimental parameters, sampling patterns, and constraints defines a set of experiments that is limited to a volume of a hyperspace defined by the set of experimental parameters. Parameters can be grouped by type such that grouped parameters are constrained to perform a common role in the set of experiments. The practicability of the experiment design can be estimated based on the number of experiments in the set of experiments. The experiment design can be used to prepare one or more combinatorial libraries.

74 Claims, 13 Drawing Sheets

OTHER PUBLICATIONS

R. A. Houghten "Parallel array and mixture–based synthetic combinatorial chemistry: tools for the next millennium", Annu. Rev. Pharmocol. Toxicol. (2000) vol. 40, pp. 273–282.

H. Koinuma, T. Koida, T. Ohnishi, D. Komiyama, M. Lippmaa, M. Kawasaki, "Parallel fabrication of artificially designed superlattices by combinatorial laser MBE", Appl. Phys. A 69 Supp., (1999) S29–S31.

B. Yan, L. Liu, C. A. Astor and Q. Tang, "Determination of the absolute amount of resin–bound hydroxyl or carboxyl groups for the optimization of solid–phase combinatorial and parallel organic synthesis", Anal. Chem. (1999) vol. 71, pp. 4564–4571.

SAS Institute, "*JMP Statistical Discovery Software: Design of Experiments*", 2000, Version 4.

James N. Cawse, Ph.D., "*Experimental Strategies for Combinatorial and High–Throughput Materials Development*", Accounts of Chemical Research, 2001, vol. 34, No. 3, pp. 213–221.

L. A. Corkan et al., "*Application of an Automated Chemistry Workstation to Problems in Synthetic Chemistry*", Chemometrics and Intelligent Laboratory Systems: Lab. Info. Mgmt., 1992, vol. 17, pp. 95–105.

L. A. Corkan and J. S. Lindsey, "*Design Concepts for Synthetic Chemistry Workstations*", Advances in Laboratory Automation Robotics, 1990, vol. 6, pp. 447–497.

L. A. Corkan and J. S. Lindsey, "*Experiment Manager Software for an Automated Chemistry Workstation, Including a Scheduler for Parallel Experimentation*", Chemometrics and Intelligent Laboratory Systems; Lab. Info. Mgmt., 1992, vol. 17, pp. 47–47.

M. W. Deem, "*A Statistical Mechanical Approach to Combinatorial Chemistry*", Advances in Chemical Engineering 28, Academic Press, 2001, pp. 81–121.

M. Falcioni and M. W. Deem, "*Library Design in Combinatorial Chemistry by Monte Carlo Methods*", Phys. Rev. E61, 2000, pp. 5948–5952.

J. S. Lindsey, "*Automated Workstations for Chemical Synthesis in Japan: A New Paradigm for Pharmaceutical Research*", Am. Lab., 1993, pp. 17, 18, 20.

J. S. Lindsey, "*A Retrospective on the Automation of Laboratory Synthetic Chemistry*", Chemometrics and Intelligent Laboratory Systems: Lab. Inf. Mgmt., 1992, vol. 17, pp. 15–45.

J. S. Lindsey and L. A. Corkan, "*Toward High–Performance Parallel Experimentation Machines: Use of a Scheduler as a Quantitative Computer–Aided Design Tool for Evaluating Workstation Performance*", Chemometrics and Intelligent Laboratory Systems: Lab. Info. Mgmt., 1993, vol. 21, pp. 139–150.

A. M. Thayer, "*Bioinformatics for the Masses*", Business, 2000, vol. 78, No. 6, Cenear 78, pp. 19–32.

Briceno et al., Science 270, pp. 273–275, 1995.

Maier, "Combinatorial Chemistry–Challenge and Chancer for the Development of New Catalysts and Materials," Agnew. Chem. Int. Ed., 1999,38, 1216..

Thayer, Chem. Eng. News, Feb. 12, 1996 pp. 57–64.

| | | | | | | |
|---:|---:|---:|---:|---:|---:|---:|
| 70.0000 | 0.0000 | 0.0000 | 10.0000 | 0.0000 | 20.0000 | 0.0000 |
| 60.0000 | 10.0000 | 0.0000 | 10.0000 | 0.0000 | 20.0000 | 0.0000 |
| 50.0000 | 20.0000 | 0.0000 | 10.0000 | 0.0000 | 20.0000 | 0.0000 |
| 40.0000 | 30.0000 | 0.0000 | 10.0000 | 0.0000 | 20.0000 | 0.0000 |
| 30.0000 | 40.0000 | 0.0000 | 10.0000 | 0.0000 | 20.0000 | 0.0000 |
| 20.0000 | 50.0000 | 0.0000 | 10.0000 | 0.0000 | 20.0000 | 0.0000 |
| 10.0000 | 60.0000 | 0.0000 | 10.0000 | 0.0000 | 20.0000 | 0.0000 |
| 0.0000 | 70.0000 | 0.0000 | 10.0000 | 0.0000 | 20.0000 | 0.0000 |
| 60.0000 | 0.0000 | 10.0000 | 10.0000 | 0.0000 | 20.0000 | 0.0000 |
| 0.0000 | 60.0000 | 10.0000 | 10.0000 | 0.0000 | 20.0000 | 0.0000 |
| 50.0000 | 0.0000 | 20.0000 | 10.0000 | 0.0000 | 20.0000 | 0.0000 |
| 0.0000 | 50.0000 | 20.0000 | 10.0000 | 0.0000 | 20.0000 | 0.0000 |
| 40.0000 | 0.0000 | 30.0000 | 10.0000 | 0.0000 | 20.0000 | 0.0000 |
| 0.0000 | 40.0000 | 30.0000 | 10.0000 | 0.0000 | 20.0000 | 0.0000 |
| 30.0000 | 0.0000 | 40.0000 | 10.0000 | 0.0000 | 20.0000 | 0.0000 |
| 0.0000 | 30.0000 | 40.0000 | 10.0000 | 0.0000 | 20.0000 | 0.0000 |
| 20.0000 | 0.0000 | 50.0000 | 10.0000 | 0.0000 | 20.0000 | 0.0000 |
| 0.0000 | 20.0000 | 50.0000 | 10.0000 | 0.0000 | 20.0000 | 0.0000 |
| 10.0000 | 0.0000 | 60.0000 | 10.0000 | 0.0000 | 20.0000 | 0.0000 |
| 0.0000 | 10.0000 | 60.0000 | 10.0000 | 0.0000 | 20.0000 | 0.0000 |
| 0.0000 | 0.0000 | 70.0000 | 10.0000 | 0.0000 | 20.0000 | 0.0000 |
| 60.0000 | 0.0000 | 0.0000 | 20.0000 | 0.0000 | 20.0000 | 0.0000 |
| 50.0000 | 10.0000 | 0.0000 | 20.0000 | 0.0000 | 20.0000 | 0.0000 |
| 40.0000 | 20.0000 | 0.0000 | 20.0000 | 0.0000 | 20.0000 | 0.0000 |
| 30.0000 | 30.0000 | 0.0000 | 20.0000 | 0.0000 | 20.0000 | 0.0000 |

FIG. 10

COMBINATORIAL PARAMETER SPACE EXPERIMENT DESIGN

CROSS-REFERENCE TO RELATED APPLICATIONS,

This application claims the benefit of U.S. Provisional Application No. 60/198,208, filed April 19, 2000, which is incorporated by reference herein.

STATEMENT REGARDING FEDERALLY SPONSORED RESEARCH

The U.S. Government has a paid-up license in this invention and the right in limited circumstances to require the patent owner to license others on reasonable terms as provided for by the terms of contract No. N00014-98-C-0288 awarded by the Office of Naval Research.

BACKGROUND

This invention relates to methods and apparatus for designing combinatorial experiments. There is currently a tremendous amount of activity directed toward the discovery and optimization of materials such as superconductors, zeolites, magnetic materials, phosphors, catalysts, thermoelectric materials, high and low dielectric materials, polymers, pharmacological compounds, semiconducting solids, and the like. These new materials are typically useful because they possess desirable levels of one or more superior physical (or other) characteristics, such as, for example, electrical conductivity, color, bio-inertness, fabrication cost, or any other property. A variety of fields (such as pharmacology, chemistry, materials science) focus on the development of new materials with superior properties. Unfortunately, even though the chemistry of both small molecules and extended solids has been extensively explored, few general principles have emerged that allow one to predict with certainty the composition, structure, and reaction pathways for synthesis of such materials. New materials are typically discovered through experimentation, rather than designed from existing principles.

A common challenge is understanding how two materials actually differ from each other. Any two materials might be similar in one or many ways (e.g. composition) but different in many other ways. Thus, one material may possess characteristics that are "better" (for a particular purpose) than those of another material for any number of reasons. One goal of experimental science is determining how the characteristics that define a material's behavior—which can be referred to as the material's "properties") vary in response to changes in a variety of conditions such as concentration or amount of different chemical components of the material, processing temperature, pressure, annealing time, molecular weight, exposure time to radiation, or the like. These conditions can be referred to as parameters (or factors) and can generally include any variable whose value can change in a continuous or discontinuous fashion. Experimental studies typically examine the variation of a given property (e.g., smell) with a measured parameter (e.g., molecular weight), often with the implicit assumption that all other parameters are held constant (i.e., their values are identical for the compared samples). In the ideal case, two materials only differ by one parameter, and variation in the measured property is construed to be caused by variation in this parameter.

Unfortunately, it is impossible to completely determine how two materials are "different". While variation in a given parameter (e.g., chemical composition) might be fairly obvious (one sample has 20% more nitrogen than the other), variation in another parameter might remain hidden (one sample has a slightly preferred grain orientation, vs. another sample's random orientation). The challenge is determining which parameters have a significant effect on the property of interest. This challenge requires the examination of the effects of many different parameters on the desired properties. Variation in each of these parameters creates a parameter space: a hyperspace bounded by all the relevant parameters that describe a material. A single material is thus defined by its coordinates within this parameter space—the values for each of these parameters for the given material. The goal of materials development is finding the coordinates of the material with the best set of desired properties. The commonly used analogy "looking for a needle in a haystack" can loosely describe this process: the parameter space is the "haystack", and the material(s) with the best set of properties is(are) the needle(s).

The process of deciding where in the parameter space to make and measure samples is called "sampling" or "populating" the parameter space. Traditionally, the discovery and development of various materials has predominantly been a trial and error process carried out by scientists who generate one experiment at a time—in other words, each axis in the parameter space is sampled serially. This process suffers from low success rates, long time lines, and high costs, particularly as the desired materials increase in complexity. Nevertheless, these methods have been successful for developing materials whose properties are governed by a relatively small number of parameters.

One set of techniques, which can be categorized under the general lable of "Design of Experiments" ("DOE") has departed from this serial sampling model. Most such techniques are predicated on an a priori assumption of smoothness in the response surface (i.e., that the response surface can be approximated by a smooth function such as a linear or quadratic equation). As a result of this presumed smoothness, a limited number of levels for each factor (e.g., 2 or 3 levels), possibly combined with statistical analyses, is assumed to be sufficient to estimate the behavior of the response surface. Other types of DOE methods can generate relatively large (by typical DOE standards) numbers of experimental points. So-called "fill factorial" designs enable users to select larger number of levels, thereby creating a grid sampling of the desired parameter space. However, because they are not constrained by the "smoothness" assumption discussed above, these methods typically simplify the experiment design by restricting the number of factors to a modest number (e.g., fewer than 10). In either case, DOE techniques typically limit sampling to a constant precision (number of levels), and offer only relatively simple constraints on factors. Using these assumptions, typical DOE techniques can be applicable to systems including a moderate number (e.g., up to 10) factors, for which a relatively small number of experiments can yield the optimum values. To put these numbers in context, a typical DOE set of experiments might investigate 5 factors, each of which takes two levels, requiring $2^5=32$ experiments, which may be distributed throughout the parameter space, rather than simply arrayed along one or more of the parameter axes.

However, many properties can be a function of a large number of different, often unknown parameters. Additionally, the combined effects of parameter variation (particularly in complex chemical and/or materials systems) can be much more complicated than the discrete effects of varying one or two parameters by themselves, resulting in a response surface that is extremely jagged, nonlinear, or similarly varying in unknown, unpredictable ways. For such systems, a very large parameter space must be precisely examined in order to identify the material with the best properties. As a result, the discovery of new materials often depends largely on the ability to synthesize and analyze large numbers of new compounds over a very broad parameter space. For example, one commentator has noted that to search the system of organic compounds of up to thirty atoms drawn from just five elements—C, O, N, S and H—would require preparing a library of roughly $10^{63}$ samples (an amount that, at just 1 mg each, is estimated to require a total mass of approximately $10^{60}$ grams—roughly the mass of $10^{27}$ suns). See W. F. Maier, "Combinatorial Chemistry- Challenge and Chance for the Development of New Catalysts and Materials," Angew. Chem. Int. Ed., 1999, 38, p. 1216. When materials characteristics vary as a function of process conditions as well as composition, the search becomes correspondingly more complex. One approach to the preparation and analysis of such large numbers of compounds has been the application of combinatorial methods.

In general, combinatorics refers to the process of creating vast numbers of discrete, diverse samples, by varying a set of starting parameters in all possible combinations. Since its introduction into the bio- and pharmaceutical industries in the late 80's, it has dramatically sped up the drug discovery process and is now becoming a standard practice in those industries. See, e.g., Chem. Eng. News, Feb.12,1996. Only recently have combinatorial techniques been successfully applied to the preparation of materials outside of these fields. See, e.g., E. Danielson et al., SCIENCE 279, pp. 837–839; E. Danielson et al., NATURE 389, by pp. 944–948, 1997; G. Briceno et al., SCIENCE 270, pp. 273–275, 1995; X. D. Xiang et al., SCIENCE 268, 1738–1740,1995. By using various rapid deposition techniques, array-addressing strategies, and processing conditions, it is now possible to generate hundreds to thousands of diverse materials on a substrate of only a few square inches. These materials include, e.g., high Tc superconductors, magnetoresistors, and phosphors. Using these techniques, it is now possible to create large libraries of chemically diverse compounds or materials, including biomaterials, organics, inorganics, internmetallics, metal alloys, and ceramics, using a variety of sputtering, ablation, evaporation, and liquid dispensing systems as disclosed, for example, in U.S. Pat. No. 5,959, 297, 6,004,617 and 6,030,917, each of which is incorporated by reference herein.

However, while existing experiment design techniques may be suited for more limited uses, such as optimization of processes that are relatively well-understood, such techniques are ill-equipped to address the vast parameter spaces, irregular response surfaces and large libraries typical of these combinatorial techniques. Accordingly, there is a need for techniques for designing combinatorial experiments that address such concerns.

SUMMARY

The invention provides methods and apparatus for populating a multidimensional experimental parameter space with points corresponding to candidate materials. In general, in one aspect, the invention features methods, systems and apparatus, including computer program apparatus, implementing techniques for designing a set of experiments. The techniques can include defining a set of experimental parameters, one or more sampling patterns defining a sampling of each parameter of the set of experimental parameters, and one or more constraints limiting the set of experiments to a particular volume or volumes of a hyperspace defined by the set of experimental parameters; generating a first estimate of the practicability of a set of experiments; providing the estimate to a user; receiving an input in response to the estimate; in response to an input modifying the set of parameters, sampling patterns or constraints, generating a second estimate of the practicability of the set of experiments and providing the second estimate to the user; and in response to an input approving of the estimate, generating an experiment design including a final set of experiments defined by the parameters, the sampling patterns and the constraints. A plurality of the set of parameters can be grouped according to a parameter type such that the grouped parameters are constrained to perform a common role in the set of experiments. Practicability estimates can include a count of the number of experiments in the set of experiments.

Particular implementations can include one or more of the following features. The experiment design can be translated from the hyperspace defined by the set of experimental parameters onto planes representing arrays of one or more combinatorial libraries. The experiment design can include data representing a plurality of sets of coordinates in the hyperspace defined by the set of experimental parameters. Each of the sets of coordinates can define an experiment in the final set of experiments. The experiment design can be implemented to cause a computer-controlled combinatorial synthesis process to perform the final set of experiments. The sampling patterns can include a first sampling pattern defined for a first parameter of the set of experimental parameters and a second sampling pattern defined for a second parameter of the set of experimental parameters, such that the first sampling pattern is different from the second sampling pattern. The sampling patterns can include a gradient of parameter values defined by a minimum parameter value, a maximum parameter value and a step size. The set of experimental parameters can include a plurality of component materials to be used in the set of experiments, as well as one or more process condition to be varied in the set of experiments.

The constraints can include mixture constraints limiting the fractional contribution of component materials to a total composition in the experiments. Mixture constraints can specify minimum and/or maximum numbers of component materials to be included in the experiments. The constraints can include type constraints limiting the total number of parameters of a specified type to be included in the experiments. The constraints can include a sum constraint limiting the sum of a contribution of parameters of a specified type to the experiments. The constraints can include balance constraints limiting the contribution of specified parameters to the experiments based on the contribution of other parameters. The constraints can include list constraints identifying a list of starting compositions to be used to generate the set of experiments. Each of the starting compositions can be represented as a point in the hyperspace defined by the set of experimental parameters, and list constraints can specify a distance criterion setting an acceptable distance in the hyperspace from the points corresponding to the starting compositions. Starting compositions can be derived from results of previous experiments. The constraints can include synthesis constraints specifying an order, including a variable order, in which component materials are to be added in a synthesis to be performed during the experiments. The constraints can include process constraints specifying an order, including a variable order, in which process steps are to be performed in during the experiments. The constraints can include project constraints specifying the order in which particular experiments should be performed. Project constraints can assign priority values to particular parameters, representing a relative priority attached to the corresponding parameter. The constraints can include chemistry-specific constraints such as balance constraints, electron-counting constraints, atomic size constraints, ionic size constraints, atomic packing constraints, ionic packing constraints, heat of formation constraints, or entropy constraints. The constraints can include tolerance values representing an amount by which the constraints can be relaxed during generation of the experiment design.

The set of experiments can be defined by counting through parameter space points defined by the experimental parameters and the sampling pattern and applying the experimental constraints to the parameter space points. The set of experimental parameters can include four, six, ten, or fifty or more parameters. The sets of experiments can include 48, 96, 1,000, 10,000, 50,000 or 100,000 or more experiments. The component materials can have an associated set of material properties, which can include, for example, molecular weight, equivalents, density and concentration. Defining the experimental parameters can include receiving sets of values for one or more of the material properties associated with any component materials.

In general, in another embodiment, the invention features methods and apparatus, including computer program apparatus, implementing techniques for designing a set of experiments. The techniques can include defining a set of experimental parameters, one or more sampling patterns defining a sampling of each parameter of the set of experimental parameters, and one or more constraints limiting the set of experiments to a particular volume or volumes of a hyperspace defined by the set of experimental parameters, and generating an experiment design defined by the parameters, the sampling patterns and the constraints. At least a plurality of the set of parameters can be mixture parameters defining a plurality of component materials to be used in the set of experiments to generate a mixture. The sampling patterns defined for the mixture parameters can define a non-uniform sampling of the mixture parameters. The constraints can include a mixture constraint limiting the fractional contribution of at least a plurality of the component materials to a total composition in one or more of the experiments in the set of experiments. The constraints can include a balance constraint limiting the contribution of at least one of the mixture parameters to the experiment design based on the contribution of a plurality of other mixture parameters to one or more of the experiments in the set of experiments. Mixture constraints can include one Or more tolerance values representing an amount by which the mixture constraint can be relaxed during generation of an experiment design.

In general, in another embodiment, the invention features methods and apparatus, including computer program apparatus, implementing techniques for designing a set of experiments. The techniques can include: defining a set of experimental parameters and identifying the parameters to an experiment design system; selecting one or more sampling patterns defining a sampling for each of the parameters and providing the sampling patterns as input to the system; defining one or more constraints limiting experiments in the set of experiments to a particular volume or volumes of a hyperspace defined by the set of experimental parameters and providing the definition of the constraints to the system; receiving from the system an estimate of the practicability of the set of experiments defined by the parameters, the sampling patterns and the constraints; if the estimate indicates that the set of experiments is not practicable, modifying at least one of the set of parameters, the sampling patterns or the constraints, and receiving a second estimate of the practicability of the set of experiments; and if the estimate indicates that the set of experiments is practicable, approving of the estimate, and generating an experiment design defined by the parameters, the sampling patterns and the constraints. The set of experimental parameters can include at least four mixture parameters. Each of the mixture parameters can be associated with a component material to be used in the set of experiments. Each of a plurality of the set of experiments can include the formation of a mixture of the component materials and the reaction of the mixture to form a product. The first estimate can include a count of the set of experiments defined by the set of experimental parameters, the sets of values and the constraints. The experiment design can define one or more combinatorial libraries of materials including a plurality of members. Each of a plurality of the members can correspond to a different experiment of the set of experiments and can include a different mixture of the at least four component materials associated with the mixture parameters. The experiment design can provide for the mixture of each of the component materials before the reaction of the component materials to form the product.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A and 4B illustrate embodiments of a design interface for defining component materials to be used in designing a set of experiments.

FIG. 10 illustrates an embodiment of a design properties interface identifying a set of parameter space points identified by a design program.

Like reference symbols in the various drawings indicate like elements.

DETAILED DESCRIPTION

Figure 1:
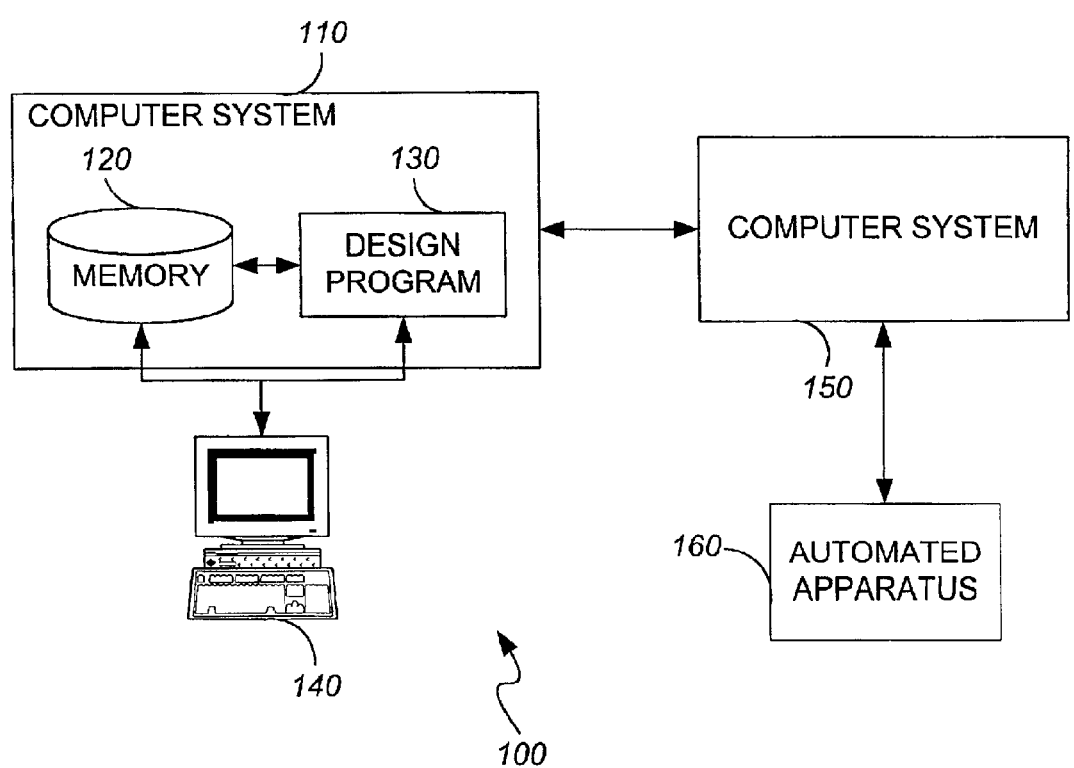
FIG. 1 is a block diagram illustrating a system for computer-implemented population of combinatorial parameter space.

The invention relates to methods and apparatus for designing a set of experiments to identify materials having desirable physical characteristics. As described above, the value of any material stems from a set of physical characteristics required to fulfill a need. In this specification, these characteristics are referred to as "properties". A property is a quantifiable, intrinsic characteristic of a material. A material's properties can include, for example, superconductivity, magnetoresistance, luminescence, fluorescence, binding specificity, sensor response, or catalytic or enzymatic activity to name just a few. In general, a material's properties can be measured experimentally and are a function of other, known, characteristics of the material, which, in this specification, will be referred to as "parameters".

A parameter is a quantifiable extrinsic variable, whose variation leads to a change in a given property (the changes resulting from variation in the parameter sometimes being referred to as a "response"). According to this definition, parameters can include, for example, process parameters such as temperature, pressure, pH, and exposure time, as well as physical parameters such as composition (including fractional or relative composition of a particular component material), molecular weight, and grain size. While there can be overlap between properties and parameters, for the purposes of this specification, it is assumed that parameters can be controlled as inputs in the experimental process, whereas properties are what results. The set of parameters affecting a given property can be analogized to boundaries in a multidimensional parameter space or volume, with a given set of parameter values defining a unique point in the parameter space corresponding to a set of physical and process conditions.

In traditional experimental science, the relationship between parameters and properties is tested using experiments designed so that Property (i) is to be measured as a function of Parameter (x), with all other parameters held constant. The critical implicit assumption is "all other parameters held constant". If this condition is true, the variation of (i) is only a function of the variation of (x). In this case, the experimental results can be reported as a two-dimensional plot of values for Property (i) as a function of Parameter (x); this lack of variation in all other parameters that affect (i) means that the experimental results are a slice through the parameter space along the (x) axis that is orthogonal to all other parameter axes.

In reality, however, it is difficult to conduct an experiment in which all other parameters do not vary. If, despite all efforts to the contrary, Parameter (y) also changes during the experiment, the response of Property (i) is a function of the variation in both (x) and (y). As a result, the two dimensional notion of experimental results (a plot of (i) vs. (x) as discussed above) breaks down; instead, the observed relationship between (i) and (x) is really a projection in the parameter space, with the variation in (y) compressed into the (i) vs. (x) plot. Good traditional experimental studies are accordingly those in which the real measured variation in response of (i) is due primarily to variation in (x)—that is, the scientist succeeds in keeping other parameters constant during the experiment. Further experimentation (e.g., (i) vs. (y)) examines the response of (i) with respect to the remaining parameters, eventually yielding a multidimensional response model constructed from two-dimensional projections of the parameter space.

However, the extrapolation of multidimensional relationships from two dimensions of data results in a fundamental loss of information as the parameter space volume is compressed in to a series of two-dimensional projections. For phenomena in which the interactions among parameters are complex, the response of (i) in the high-dimensional volume can be poorly predicted by projections in lower dimensions. As a result, combinatorial experiments based on low-dimensional libraries are an inefficient way to search for a target property.

The goal of a successful combinatorial experiment is therefore the efficient search of points in an N-dimensional parameter space whose volume and dimensionality are unknown. This conceptualization is fundamentally different from classical experimentation, which attempts to generalize two-dimensional slices through parameter space but actually generates projections of the space. Early efforts at combinatorial experiment design added the concept of dimensionality—up to two parameters to study one property—but were still fundamnentally designed to produce slices or projections through the parameter space in which all but one parameter were (hopefully) held constant.

Efficient exploration of high dimensional parameter space requires choosing experimental points for maximum information content. This requirement cannot be achieved by basing experiments on projections—regardless of dimensionality of the projection. The parameter space must be treated as a volume, and the choice of experiments must efficiently populate this volume.

The foregoing combinatorial design techniques can be implemented using an experiment design system 100 as shown in FIG. 1. Design system 100 includes a general-purpose programmable digital computer system 110 of conventional construction, including a memory 120 and a processor for running a design program 130. Design system 100 also includes input/output devices 140, and, optionally, conventional communications hardware and software by which computer system 110 can be connected to other computer systems, such as a computer system 150 controlling automated materials handling apparatus 160 (e.g., a synthesis robot, vapor deposition equipment or the like). In some implementations, design program 130 implements a graphical user interface that is displayed to a user over a display device such as a monitor. Optionally, system 100 can be implemented as part of a system for designing and preparing libraries of materials, such as is described in U.S. Provisional Application No. 60/256,270, filed on Dec. 15, 2000, which is incorporated by reference herein. Although FIG. 1 illustrates design system 100 as being implemented on a single computer system, the functions of system 100 can be distributed across multiple computer systems, such as on a network. A typical user of system 100 is a research chemist or materials scientist.

Figure 2:
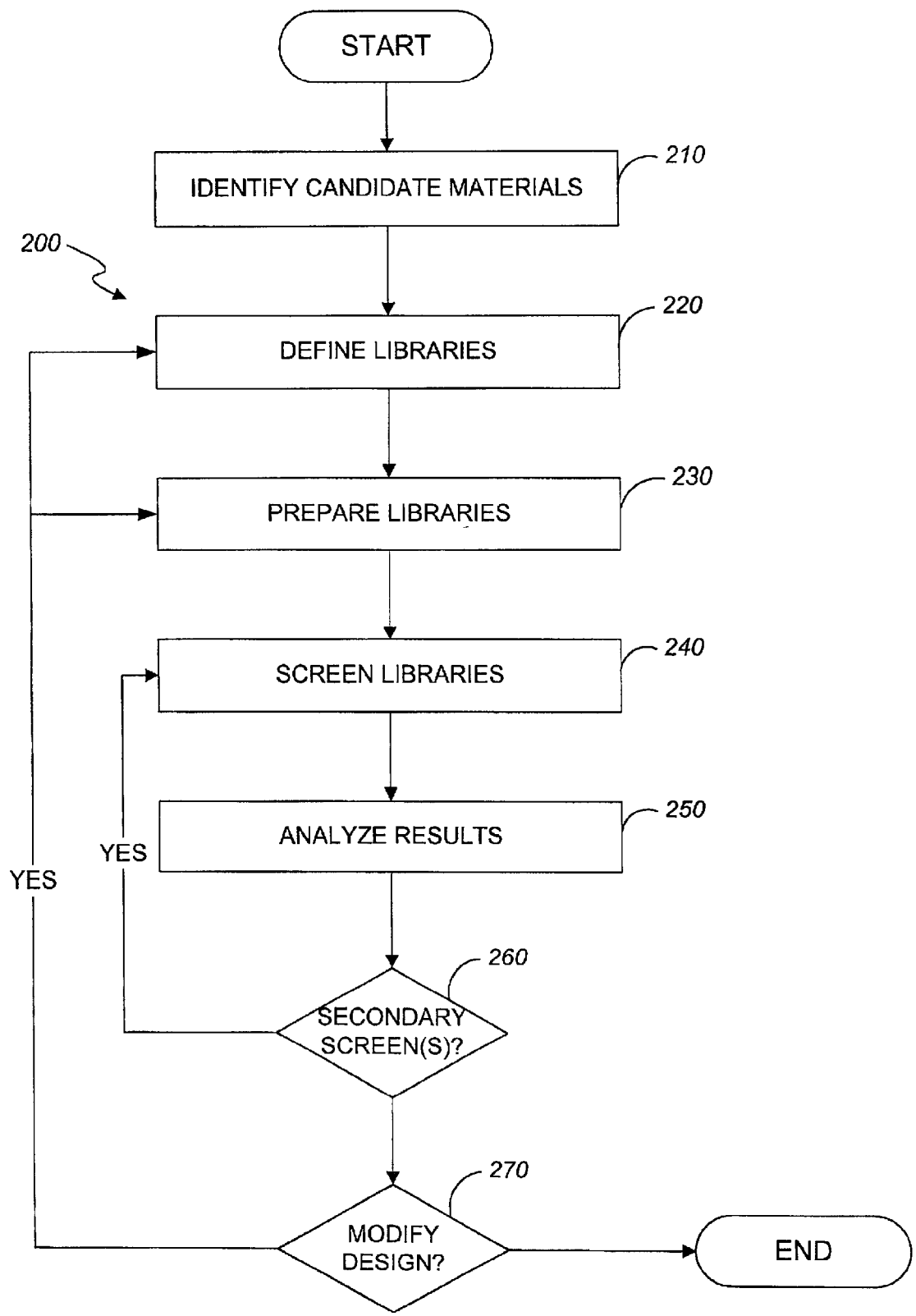
FIG. 2 is a flow diagram illustrating a combinatorial method of carrying out a set of experiments.

FIG. 2 illustrates a general combinatorial method 200 of carrying out a set of experiments as part of a combinatorial program or project to identify one or more materials having a desired property (or a desired quantity of such a property). The scientist first identifies an initial set of candidate materials to search (step 210). Next, the scientist defines one or more libraries of materials including the initial set of candidate materials (step 220). The scientist prepares this library or libraries (step 230), preferably using combinatorial synthesis techniques, and screens the library members for the desired property using high throughput screening techniques (step 240). After analyzing the screening results (step 250), the scientist may optionally submit the library or libraries (or a subset thereof) to one or more secondary screens (the YES branch of step 260)—for example, screens capable of quantifying the desired property at higher precision and accuracy, but perhaps at higher cost. The scientist may also optionally modify the experiment design (the YES branch of step 270), such as by modifying an experimental parameter (e.g., adding one or more additional component materials or by changing one or more process conditions) to generate a modified set of candidate materials, which is then submitted to steps 220 through 260 above. When the scientist identifies an acceptable material or is satisfied that all (or a sufficient number) of relevant candidate materials have been studied, the project is complete.

Design program 130 incorporates input from a variety of theoretical, numerical and physical factors, which it uses to determine a set of experiments that maximizes information content at minimum cost for each experiment. Appropriate input factors can include, for example: information from prior experiments on the phenomenon being measured; physical and chemical theory regarding the phenomenon; the expected response behavior of the phenomenon (e.g., sparsity, smoothness); the number of parameters; the expected dimensionality of the parameter space; the expected requisite sampling precision for the project (and/or for individual parameters); the overall sampling strategy (e.g., random, controlled, biased, mixed); statistical information from prior experiments; procedures for sampling modification; the availability (e.g., resource allocation) and capabilities (e.g., precision, accuracy, chemistry) of available synthesis and screening tools; and the accessibility of different dimensions in the parameter space. Design system 100 can be used both before and during a combinatorial discovery project.

Design system 100 provides a mechanism for exploring a wide variety of "what if" scenarios for project design, permitting the scientist to estimate the effects of changing chemistry, changing precision, changing sampling strategy and the like. At the beginning of a project, prior experimental work is used as an input with design system 100 to generate an initial set of experiments. Early in the process, the scientist can gauge the effect of changing composition in 7% steps vs. 5% steps or 15% steps, of adding an additional component or components to the design, and can even estimate the time the project can be expected to take to complete, given expected resource constraints. This information can inform the scientist how many different compounds should be investigated, taking into account such criteria as known chemical behavior with respect to the property of interest, the estimated length of the project, the available workforce and instrument time allocated to the project, and the maximum number of elements simultaneously present in the compounds of interest.

As the project progresses, feedback mechanisms between synthesis, screening and search strategy are combined to determine future experiments. At this later stage, design system 100 can be used to inform the scientist whether the search strategy can be modified to increase hits or throughput, whether the parameter space can be reduced without appreciable information loss, and whether the precision of the response (i.e., hit precision) matches the precision of the synthesis and screening apparatus used to implement the experimental design (i.e., oversampling or undersampling), as well as identifying how to expand the project around a particular point of interest in the parameter space.

As a brief example, thermoelectric materials could be ternary compounds including a transition metal (for example elements of Group VI or greater), a "left hand side element" such as a Group II or III element, and a "p-block" element, such as an element of Group VI or Group VII. These general categories define three "types" to which individual elements of candidate thermoelectric materials belong (although it is possible for one element to belong to more than one type). Thus, for example, a scientist may have identified 5 transition metals, 5 "LHS" elements and 3 "p-block" elements of interest for a particular application. These can be referred to as types A, B and C, such that component A1 represents the first transition metal, B2 is the second LHS element and so on. If the scientist is interested only in ternary compounds $A_xB_yC_z$ (and not, for example, $A_xA_yC_z$ or $A_xB_yB_z$) and binaries of the form $A_xC_y$ and $B_xC_y$, these descriptions define the kinds of compounds the scientist might want to synthesize; what remains is to establish the maximum precision possible under given constraints of time, budget and the like. To efficiently carry out the search for these materials, the scientist must essentially answer the question: if one wants to scan the binaries and ternaries at 10% precision, how many compounds (and libraries) must be synthesized and screened?.

Figure 3:
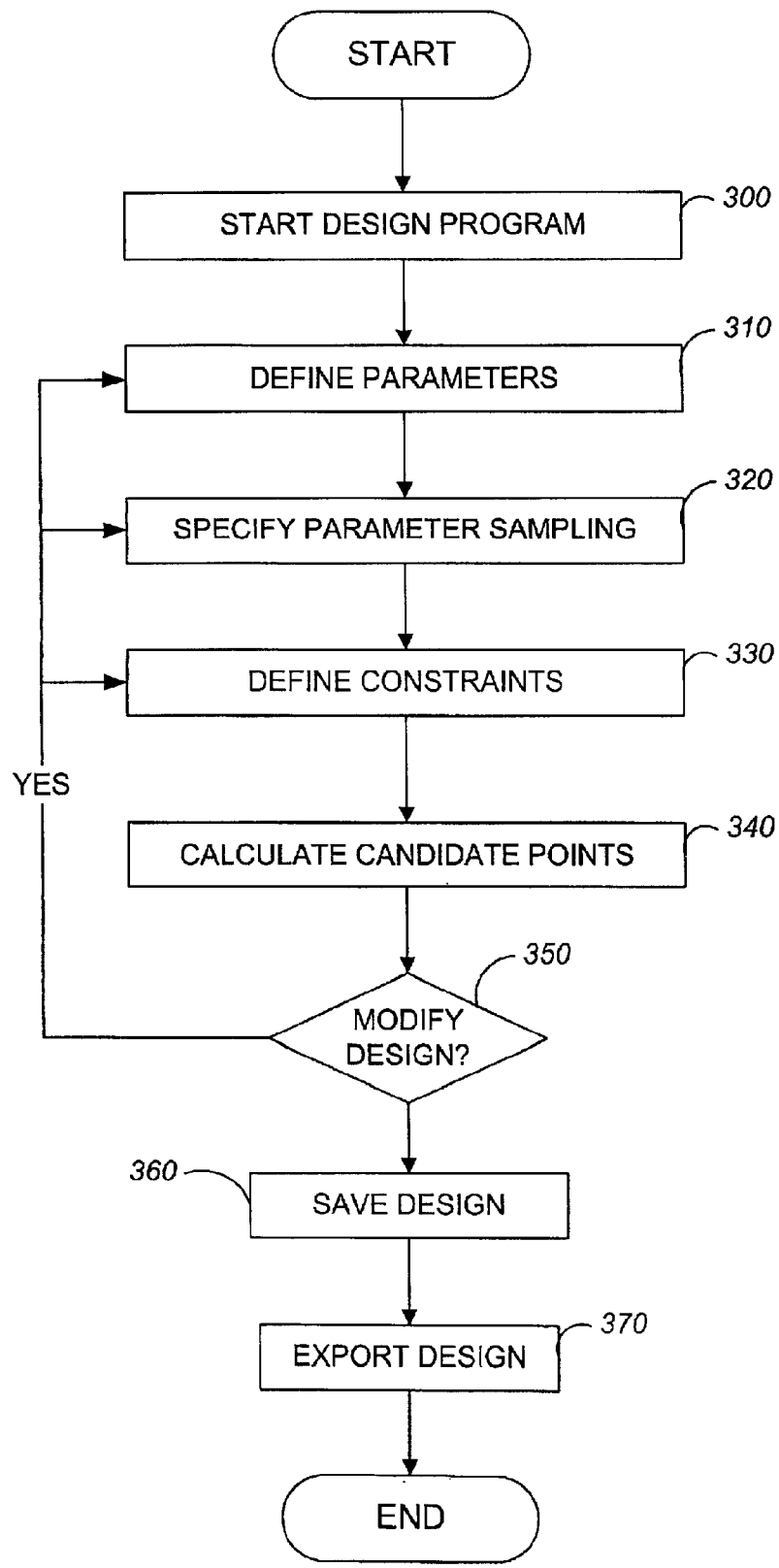
FIG. 3 is a flow diagram illustrating a method of designing a set of combinatorial experiments.

Referring to FIG. 3, the scientist accesses system 100 through I/O devices 140, starting design program 130 to begin designing a set of combinatorial experiments (step 300). Optionally, the scientist inputs information identifying the experiments (such as information identifying the scientist, a project name, and the like). The scientist defines the parameters to be used in the design (step 310), including any component materials to be used (e.g. as starting materials), process conditions, etc. For each parameter, the scientist specifies a sampling pattern (step 320). Depending on the parameter, the sampling pattern may be a variable sampling pattern—for example, a gradient (e.g., a variable composition gradient for a component material, or a process condition gradient defining such conditions as a temperature that will vary across individual experiments in the set of experiments) defined by a specified minimum value, a maximum value and a step size, from which design program 120 will calculate individual parameter values for particular experiments in the set of experiments. Depending on the nature of the parameter and the set of experiments, sampling patterns may be derived from any of a variety of different mathematical relationships, including without limitation gradients based on linear, logarithmic, exponential, polynomial or other appropriate expressions that will be apparent to those of ordinary skill in the art. Optionally, the sampling pattern can include more than one gradient, from which design program 130 will construct more complex, non-linear sampling patterns (for example, a 1% step gradient from 0 to 10% to be combined with a 10% step gradient from 10 to 100%). Alternatively (or in addition), a sampling pattern for a parameter may simply specify one or more express values for the parameter, thus fixing that parameter's absolute or relative presence in all or a portion of the project design. In a preferred implementation, the experimental parameters include a plurality of component materials to be used in preparing a mixture and the sampling pattern or patterns specified for these mixture parameters define a non-uniform sampling pattern, which may include, for example, two or more different sampling patterns associated with different mixture parameters, complex non-linear patterns for one or more such parameters as described above, or, more generally, any other sampling pattern that provides for sampling the parameter space in other than a regular (uniform) grid.

In one implementation, the user defines the parameters representing component materials to be used in the design by selecting one or more materials (e.g., chemical elements, compounds or compositions, such as stock solutions, which may themselves include one or more elements or compounds, and which may exist in a gaseous, liquid or solid phase) from a list of available materials (e.g., a chemical or inventory database) stored in memory 120. In one implementation, the user can select from available materials (or, similarly, process conditions) using a graphical interface, such as (for chemical elements) an interactive periodic table, or more generally from a dropdown list or menu of available choices. Optionally, design program 130 can present the user with chemical information concerning, e.g., the properties of a selected material, and availability information concerning, e.g., the available supply of or ordering information for the selected material. In some implementations, the user can order any desired component materials from a remote source, such as over the Internet.

Figures 4A, 4B:
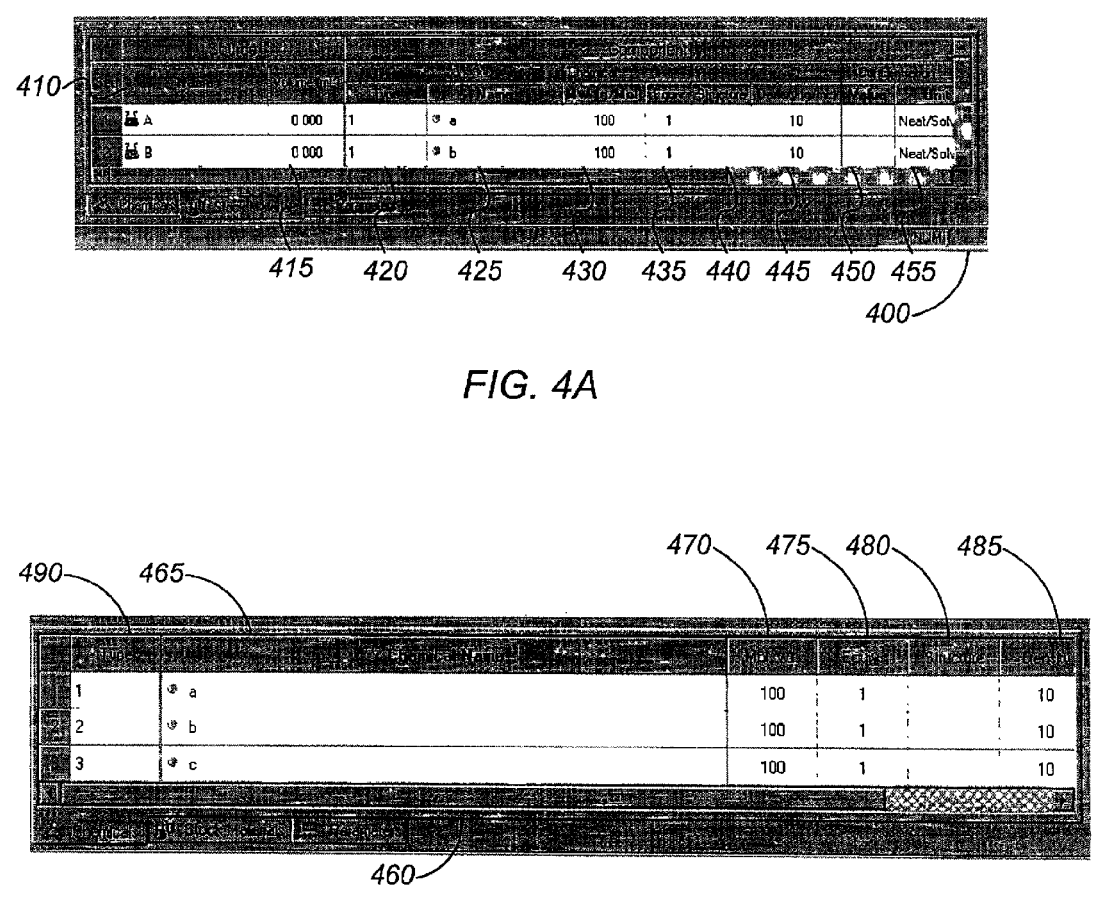

Alternatively, or in addition, the user may define additional component materials using, for example, a "Stock Materials" window 400 as illustrated in FIG. 4A. For each component material (or process condition), the user assigns a component name in field 410, and may enter information defining the component's properties, including, e.g., attributes of each constituent chemical such as type (or subtype), name (selected, for example, from a list of defined chemicals), molecular weight, equivalents, structure, density and concentration into corresponding fields 415–455. Values corresponding to component properties may be entered in any convenient units and are converted to common units for subsequent calculations by design program 130.

Similarly, individual chemicals can be defined using a "Chemicals" window 460 as illustrated in FIG. 4B. The user enters a chemical name (or selects a chemical from a graphical presentation of available chemicals such as dropdown list or menu) in Chemical Name field 465 and enters information defining the chemical's properties, such as molecular weight, equivalents, structure and density, into corresponding fields 470, 475, 480 and 485. Optionally, the user also assigns a chemical "type"—a user-selected label describing a class of chemicals that may be used as a design parameter in creating the library as will be described in more detail below—by entering a name into Type field 490. Each defined chemical type may include one or more subtypes.

The scientist defines one or more constraints to be applied to the parameter space (step 330). These constraints can include, for example, mixture constraints, composition constraints, type constraints, stoichiometric constraints, synthesis constraints, process constraints and project constraints. Mixture constraints apply to the mixing multiple component materials. Mixture constraints can ensure that the sum of the fractional composition of all component materials in a variable mixture (or portion of such a mixture) adds to 100%. Mixture constraints can also limit the total number of component materials in a given experiment returned by design program 130 (e.g., by specifying that design program 130 can return only experiments including 2, 3 or 4 component materials). Composition constraints are imposed on a group of component materials and limit the fractional amount of the group of component materials as a whole (e.g., to ensure that A and B are present as at least a specified minimum fraction of the total composition, but as no more than a specified maximum fraction). Type constraints group parameters into types (e.g., such that two parameters of the same type are not both present in individual experiments returned by design program 130). Stoichiometric constraints limit the ratio of two or more parameters (e.g., to ensure that one component material will not be present in excess relative to another component material).

In many processes, material properties can depend on the order in which component materials are added, even among materials having identical starting ingredients (or chemical formulae). Synthesis constraints specify the order in which specified component materials should be added in a synthesis. Synthesis constraints can be applied to all component materials in a mixture, or to a subset of component materials. Optionally, the user can use synthesis constraints to generate a combinatorial expansion based on the order of steps—specifying, for example, that component material A is added first and component material B is added second in one experiment, while in another, component material A is added second (or third, or fourth, etc.) in another.

More generally, process constraints allow the user to specify (or vary) the order in which process steps occur. For example, in combinatorial device design, a user may want to deposit component material A, apply heat, and then deposit component material B and apply high energy ion interaction, followed by deposition of a third component material C with a different heat treatment, etc. Likewise, in organic chemistry, polymer chemistry, or biochemistry, for example, combinatorial methods can be used to identify optimal combinations of synthesis and processing steps. Process constraints can also be used to specify or vary a process profile within a particular step or steps. Thus, for example, a process constraint can define a temperature profile specifying three temperature levels for a heating step, each having a different, defined ramp rate, holding time, etc. Design program 130 can be configured to permit users to specify process constraints graphically, by selecting a sequence of events, and/or what permutation(s) to apply among various events or groups of events, etc., using known graphical input techniques, including selecting entries from a dropdown list or menu, selecting appropriate buttons or arrows, or drawing directly (or using a graphical input tablet) in a provided input region on a monitor screen.

Project constraints specify the order in which individual experiments in a combinatorial project should be performed, allowing the user to specify that particular permutations should be given a higher priority than others. For example, the user can specify that compositions including one component material (such as Nickel) or process condition should be tested before compositions including a different component material (such as Platinum) or condition (e.g., by assigning a higher priority value to the former parameter in a drop-down menu or input field in a parameter definition screen). Project constraints allow users to attempt to increase the probability of early success of a project, or to try out a particular hypothesis, using information derived from other sources available to the user, such as chemical theory or information from previous experiments.

In one implementation, the user defines the desired constraints by selecting from a list of available constraint types using the graphical user interface implemented by design program 130—for example, by selecting from a dropdown list or menu presented on monitor 140—causing design program 130 to display corresponding constraint definition templates through which the user can define the constraint. Optionally, the available constraints include one or more chemistry-specific constraints. One such set of constraints includes balance constraints. Balance constraints can be invoked to constrain one element of a combination (e.g., a member of one group in a multi-group combination such as may be defined using a set of type constraints as discussed above and in more detail below).

Thus, for example, for a desired composition ABC that is constrained (e.g., by a mixture constraint) to yield a composition A+B+C=100%, the scientist may define a balancing constraint on component material (or group) C. Such a constraint can provide that material C is a balancing element. To identify the experiments to be included in the project, design program 130 will vary the amount of components A and B according to their specified sampling patterns and any applicable constraints, and will calculate the amount of C as 100% —A—B. Optionally, the balance constraint may provide that the balancing element must be present within a specified range (e.g., 23%<C<79%) or ranges (or, indeed, according to more complex constraints). If the calculated amount of the balancing element falls within that range, design program will accept the mixture and include C in that amount. Otherwise, design program 130 will reject the mixture as outside the scope of the applicable constraints, and will therefore exclude the point corresponding to the mixture from the experimental parameter space.

Balancing constraints can be applied to a variety of chemical characteristics, including, for example, charge, mass, partial pressure of gas mixtures, thickness of films, and the like. Other chemistry-specific constraints could include, without limitation, electron-counting rules, as well as constraints on atomic and/or ionic size relationships, atomic/ionic packing, heat of formation considerations, entropy, or other chemistry and/or material specific conditions, etc. The selection of particular chemistry-specific constraints will depend on the anticipated uses to which system 100 will be put; such constraints can be implemented using known programming techniques. Additionally, users can be permitted to create user-defined or custom templates to capture existing (or later-developed) chemical/materials knowledge, which custom templates can be made available to other users of system 100. When the scientist has defined the relevant parameters and constraints, design program 130 generates a corresponding experimental design (a combinatorial expansion) identifying a set of candidate materials (step 340)—for example, by counting through points in the parameter space corresponding to combinations of the specified parameter values and applying the specified constraints to each such point. Optionally, at this point (or at any point during the design process), design program 130 can present the user with an estimate of the number of experiments that will be required to satisfy the experimental design. In some implementations, design program 130 can be configured to automatically provide the user with information relating to the feasibility of performing a specified set of experiments. In one such implementation, design program 130 can notify the user if the time taken to calculate the combinatorial expansion for the defined set of parameters and constraints exceeds a predetermined computational threshold selected based on known or predicted relationships between the time taken to calculate a combinatorial expansion for complex parameter spaces and the time taken to perform the experiments represented by such calculations. The establishment of particular computational thresholds will depend on the nature of the chemistry and the project involved.

After reviewing the design (and/or based on a calculated estimate of the number of required experiments), the scientist can add, modify or remove parameters or constraints to the design (the YES branch of step 350) to optimize the chances of achieving a successful result given existing resource limitations and/or to determine how changes to the complexity (i.e., the number of parameters and/or dimensions) and precision (i.e., the distance between points in the experimental parameter space) affect the time and resources required to implement the design. At any time, the scientist can save the design (step 360). If desired, design program 130 can export the design (step 370), generating output in a known data format (e.g., a data file, string, or the like). Such output can include the parameter space coordinates (e.g., parameter values defined by the design for all experimental parameters) of each experimental point, and optionally other data as well, such as information relating to the component materials (e.g., chemical information supplied for specified component materials as discussed above), information relating to the physical substrates in or on which the experimental compositions are to be synthesized (e.g., dimensions of the desired substrate or substrates, volumes of each experimental composition, etc.), synthesis tool protocols, or more generally, any other information relevant to the experiment design or the synthesis/preparation of the experimental compositions in the design. The output information can be provided to a downstream library design and/or synthesis process to physically synthesize the experimental samples occupying the desired parameter space coordinates (i.e., compositions having the physical and process characteristics represented by the individual parameter space points in the design). In a preferred implementation, the design is provided to a library design system such as that described in co-pending U.S. patent application Ser. No. 09/420,334, filed Oct. 18, 1999, for implementation by robot control software such as that described in U.S. patent application Ser. No. 09/305,830, filed May 5, 1999, both of which applications are incorporated by reference herein. Alternatively, the output can be provided to any of a variety of computer-controlled materials-handling or synthesis tools for use in preparing such experimental samples under the control of device control software operating according to known programming techniques. In some implementations, the downstream library design and/or synthesis process provides information necessary to translate the experiment design into one or more combinatorial libraries, which may include some or all of the following: physical dimensions of the desired substrate or substrates on or in which the experimental compositions will be synthesized, volumes of each experimental composition, chemical inventory information, synthesis tool protocols, or other information necessary to create a physical manifestation of the desired sample. While FIG. 3 illustrates these steps in a particular order, the order is not critical; individual steps can be performed in other orders, and can be performed multiple times during design of a given set of experiments.

Figure 5:
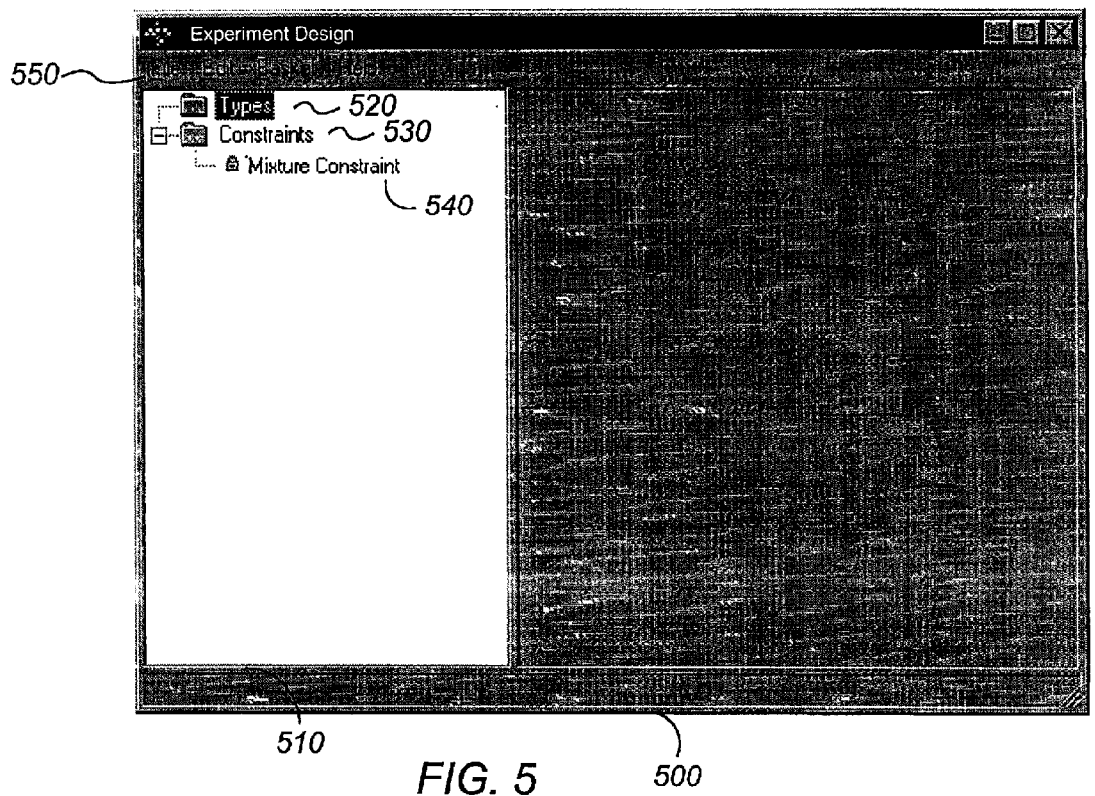
FIG. 5 illustrates an embodiment of a project design interface for designing a set of experiments.

A sample design session directed to ternary compounds of the form $A_xB_yC_z$ derived from seven component materials A1, A2, A3, B1, B2, C1 and C2 will now be described with reference to FIGS. 5–11. Referring first to FIG. 5, when the user opens a project, design program 130 generates a design interface 500 that system 100 displays over I/O devices 140. In panel 510, design program 130 displays a hierarchical list of type nodes 520 and constraint nodes 530, each of which can have one or more child nodes such as mixture constraint node 540. The user can add new parameter types or constraints by making an appropriate selection from menu bar 550, or by invoking contextual menus (accessed, for example, by "right-clicking" with a mouse 140 on the appropriate node).

Figure 6:
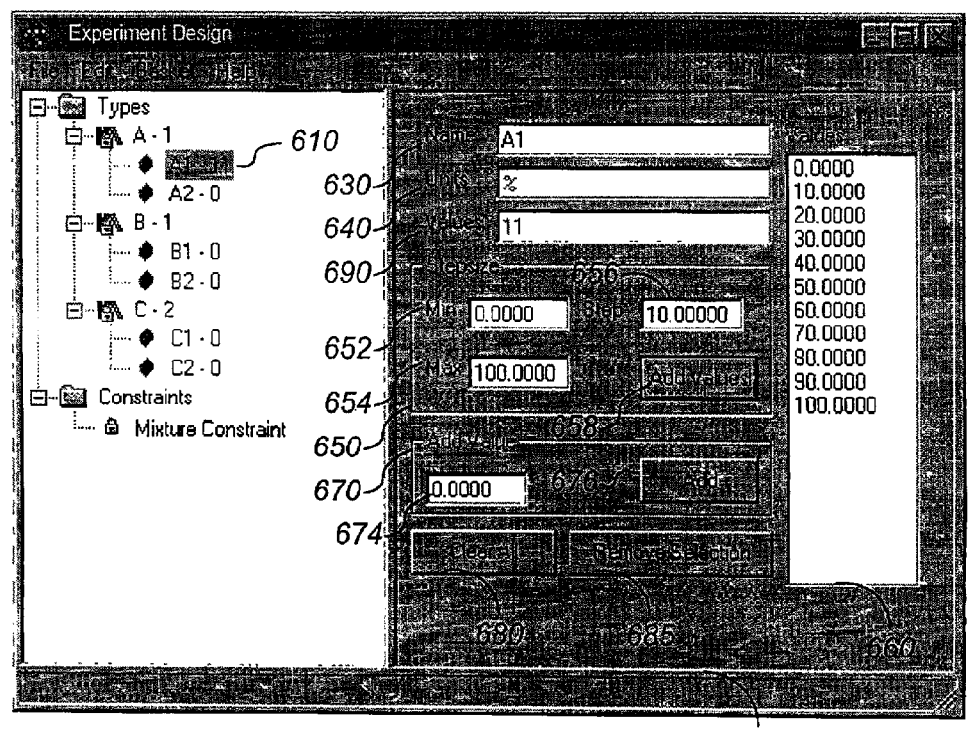
FIG. 6 illustrates an embodiment of a design interface for defining values for a selected design component.

Referring to FIG. 6, in response to the user's selection of a particular type node 610, design program 130 displays a parameter worksheet in workspace 620. The user inputs a parameter name in Name field 630, and selects desired units for sampling (such as percent of the total composition) in Units field 640. The user can define a sampling gradient in Stepsize panel 650, entering a minimum value, a maximum value and step size in fields 652, 654 and 656, respectively. After entering this information, the user selects Add Values button 658, causing design program 130 to generate a corresponding range of values for the specified parameter, which are displayed in Values list 660. The user can add specific values for the parameter in Add Value panel 670, by entering the desired value in field 674 and selecting Add button 676, causing design program 130 to add the specified value to Values list 660. At any time, the user can clear all values from Values list 660 by selecting Clear All button 680, and can remove a specific value or values from Values list 660 by selecting the values (e.g., with a mouse 140) and selecting Remove Selection button 685. In Values field 690, design program 130 displays a running total of the number of values listed in Values list 660.

Figure 7:
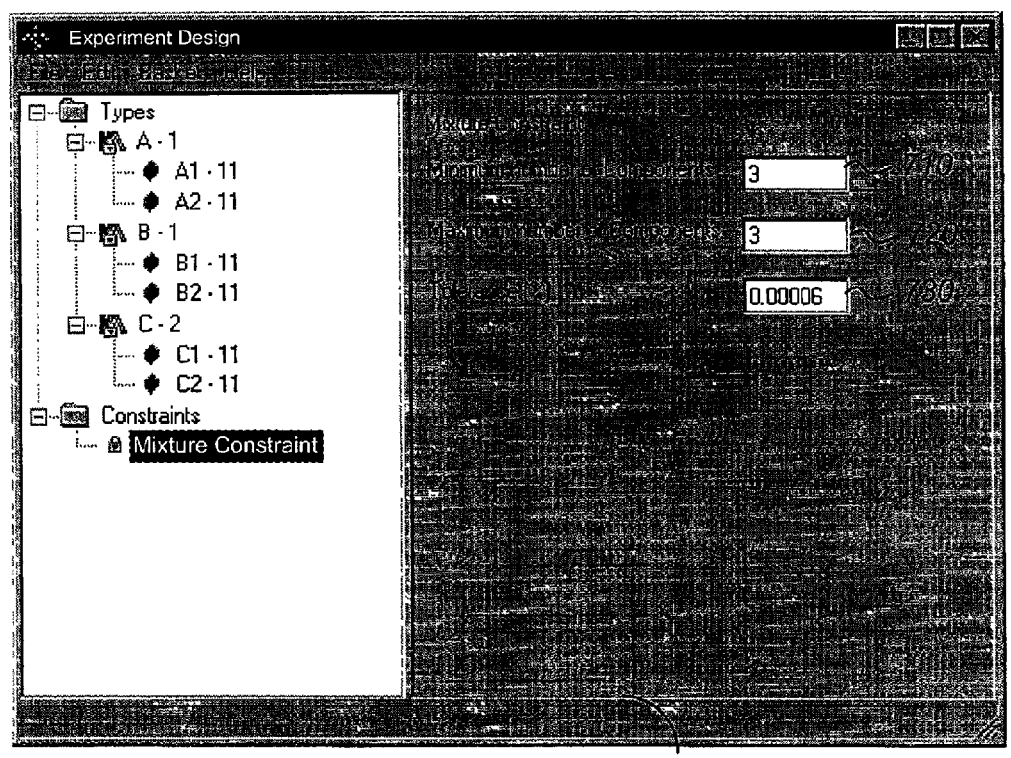
FIG. 7 illustrates an embodiment of a design interface for defining a global constraint on an experiment design.

The user defines a mixture constraint through a mixture constraint worksheet 700 as shown in FIG. 7. The user specifies a minimum number of parameters and a maximum number of parameters to be included in a variable mixture—in this ternary example, 3 each—in fields 710 and 720, respectively. The user may also enter a tolerance in field 730, which design program 130 uses to relax the mixture constraint to allow for sampling in step sizes that would otherwise be incompatible (and thereby avoid unduly excluding too many candidates to maintain a high precision). For example, assume component materials A and B are to be sampled in step sizes of 10%, while component material C is to be sampled in step sizes of 1%. In the absence of a tolerance capability, many potentially valuable candidates would be excluded by the mixture constraint that the total fractional composition of the material sum to 100%. For example, a composition in which [A]=50%, [B]=50% and [C]=1% would sum to 101% and would therefore be excluded. To avoid this potential problem, design program 130 can be configured to permit the user to input or select tolerance values that relax the mixture constraint: in the example just given, the user could select a tolerance of 5%, meaning that design program 130 would return candidates satisfying the specified constraints for which the sum of relative concentrations falls between 95 and 105%. Thus, the 50%, 50%, 1% composition specified above would be accepted as summing to 101%, within the specified tolerance. Preferably, design program 130 then performs a renormalization operation to give a final composition of A=50/101*100%=49.5%, B=50/101*100%=49.5%, C=1/101*100%=0.99%. The user can specify one tolerance value to be applied to some or all of the parameters in a set of experiments, or can select a set of tolerances, each of which may apply to one or more components individually.

A mixture constraint can be applied to all or a subset of the material parameters defined for a particular design. Any material parameters that are not included in a mixture constraint are therefore not considered by design program 130 in calculating the fractional mixture that is constrained by such a constraint to sum to 100%. Such parameters components can include, for example, materials such as additives or activators that the user wishes to add to the design in a combinatorial manner.

Figure 8:
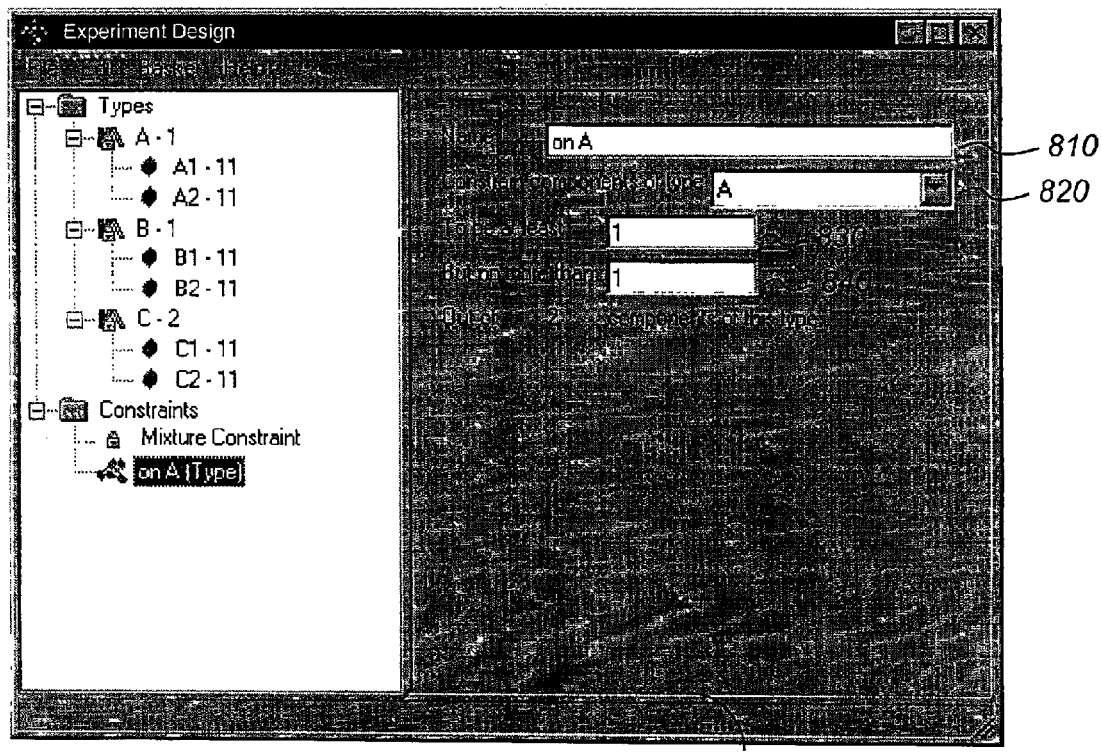
FIG. 8 illustrates an embodiment of a design interface for defining a type constraint on an experiment design.

Type constraints are defined in a type constraint worksheet 800 shown in FIG. 8. The user names the type constraint in field 810, and identifies the type to be constrained by making the appropriate selection in dropdown list 820. In fields 830 and 840, respectively, the user enters a minimum and a maximum number of parameters of the specified type to be included in the candidate materials. In the example illustrated in FIG. 8, the user's entries provide that only one parameter of type A (i.e., parameters A1, A2 and A3) can be present in the candidate materials. As a result, design program 130 will not consider points in the parameter space that include both parameter A1 and A2. Type constraints permit the user to "group" similar parameters by a variety of common features relating to the parameter's role in the set of experiments (e.g., by grouping chemicals by reactivity, valence state, function or the like). The inclusion of type constraints can streamline the process of calculating the combinatorial expansion, in essence requiring only a single calculation for all members of a given group or type, with the resulting set of experiments being permuted for each group member.

Figure 9:
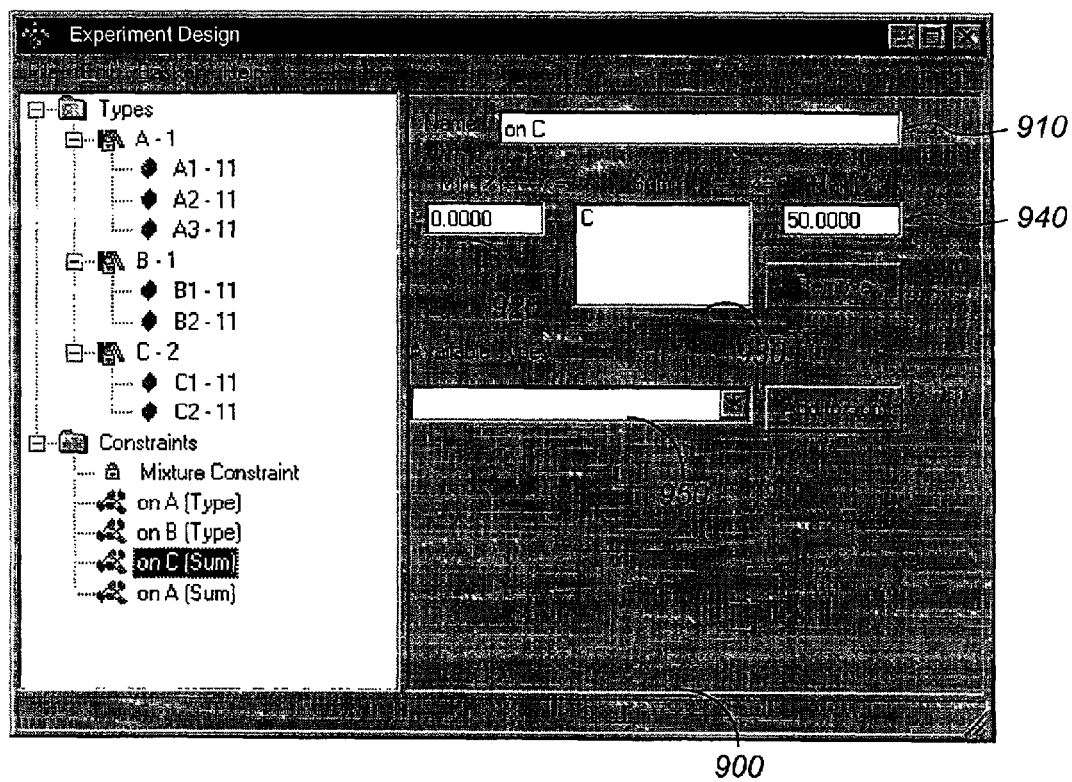
FIG. 9 illustrates an embodiment of a design interface for defining a sum constraint on an experiment design.

Similarly, the user defines a sum constraint on type C in a sum constraint worksheet 900 shown in FIG. 9. The user names the constraint in field 910, and in fields 920, 930 and 940 enters a range for the specified sum, here providing that the sum of all parameters of type C must be between 20 and 50%. Sum constraints can be imposed on individual parameters or multiple parameters as well as on types selected from dropdown list 950.

Figure 11:
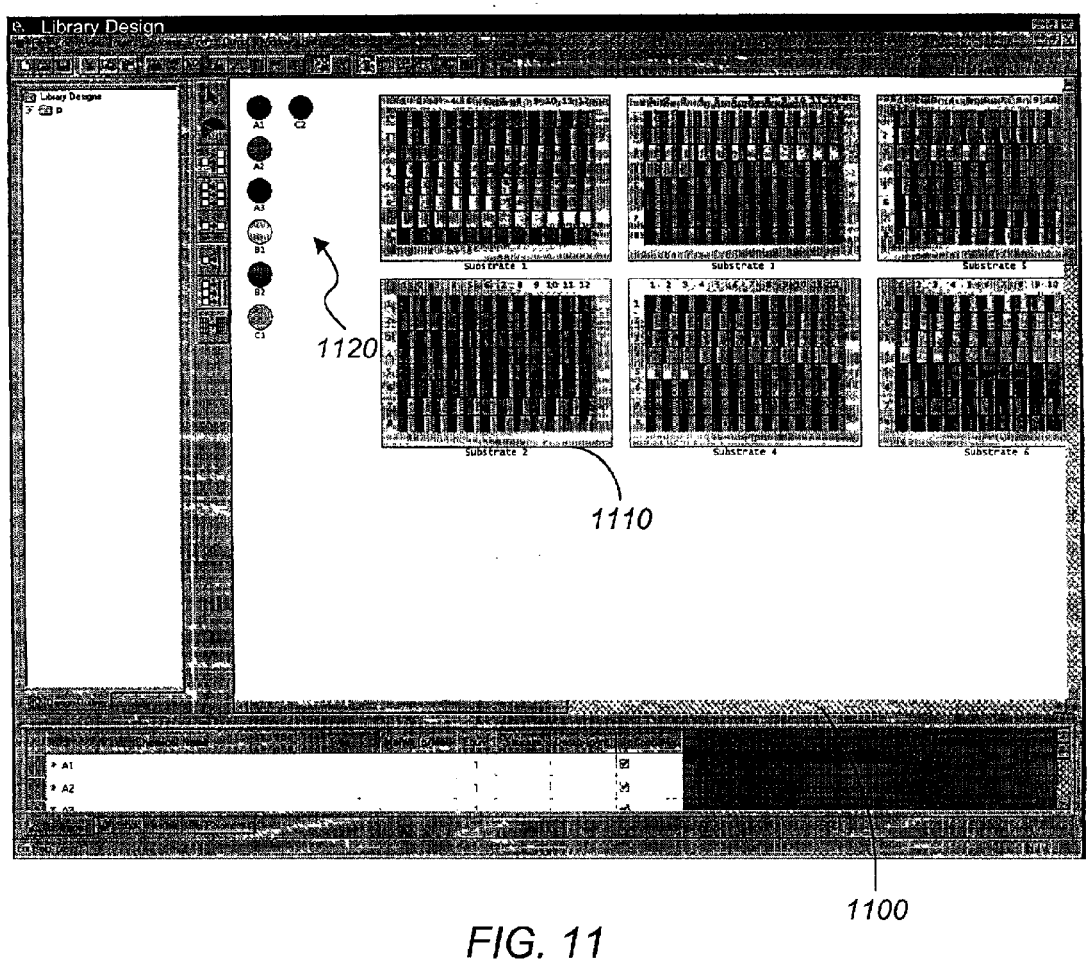
FIG. 11 illustrates an embodiment of a library design interface for generating a series of libraries corresponding to parameter space points identified by a design program.

When all parameters and constraints have been entered, the user instructs design program 130 to begin the calculation (for example, by selecting File—>Calculate Design in menu bar 550). When the calculation is complete, design program 130 returns a Design Properties window 1000 as shown in FIG. 10. The results are displayed as grid 1010, with columns corresponding to each of the specified parameters. Each entry (row) in grid 1010 corresponds to a candidate material composition identified by design program 130 in the specified parameter space. In this example, design program 130 has identified a total of 1,818 candidate materials meeting the specified constraints. The user can save the design—for example as a text file that can be read by commercially available spreadsheet applications. Alternatively, the user can save the design as a list of points and compositions in a format suitable for use by library design software such that disclosed in U.S. patent application Ser. No. 09/420,334, filed Oct. 18, 1999, which is incorporated by reference above. After receiving such a list, the library design software prompts the user to define one or more destination substrates into which the software will map the identified candidate materials (e.g., by specifying a number of rows and columns in a rectangular matrix or grid), and translates the design into a "recipe file" format that can be implemented to prepare one or more physical libraries containing the identified candidate materials as shown in FIG. 11. Optionally, the library design software (or design program 130) can also be configured to optimize the mapping step, for example, to minimize the number of materials used to prepare each physical plate. Workspace 1100 includes a series of rectangular arrays 1110, each of which represents a physical library substrate. Each individual element of arrays 1110 corresponds to a unique combination of parameters A1, A2, A3, B1, B2, C1 and C2 (represented in workspace 1100 as source wells 1120), as determined by design program 130 as described above.

In addition to applications in the initial design of a set of experiments, design system 100 can be used in the later stages of a project—for example, after some or all of an experiment design has been implemented and screened for desirable properties. In such cases, the user may wish to follow up on candidates of interest by, for example, focusing on a region of interest in the parameter space, increasing the design precision, or increasing complexity by adding more parameters or constraints. In one implementation, for example, the user can revisit the experiment design by using existing data (e.g., the compositions and primary screening results generated from an initial design) to add a list constraint to the original design. In this implementation, a list constraint is a list of composition values—such as a list of "hits" from a previous experiment that exhibit an acceptable value for a screened property—that design program 130 uses to restrict the content of a design, providing a subset of interest around which to focus a secondary screen.

In this example, an experiment directed to the identification of quaternary compounds of parameters A, B, C and D may identify d set of ten hits set out in Table 1, below.

TABLE I

| A (%) | B (%) | C (%) | D (%) |
|---|---|---|---|
| 55.0 | 20.0 | 10.0 | 15.0 |
| 60.0 | 20.0 | 05.0 | 15.0 |
| 70.0 | 15.0 | 05.0 | 10.0 |
| 65.0 | 25.0 | 05.0 | 05.0 |
| 70.0 | 20.0 | 05.0 | 05.0 |
| 55.0 | 25.0 | 05.0 | 15.0 |
| 55.0 | 30.0 | 05.0 | 10.0 |
| 60.0 | 25.0 | 05.0 | 10.0 |
| 50.0 | 30.0 | 05.0 | 15.0 |
| 65.0 | 20.0 | 05.0 | 10.0 |

Figure 12:
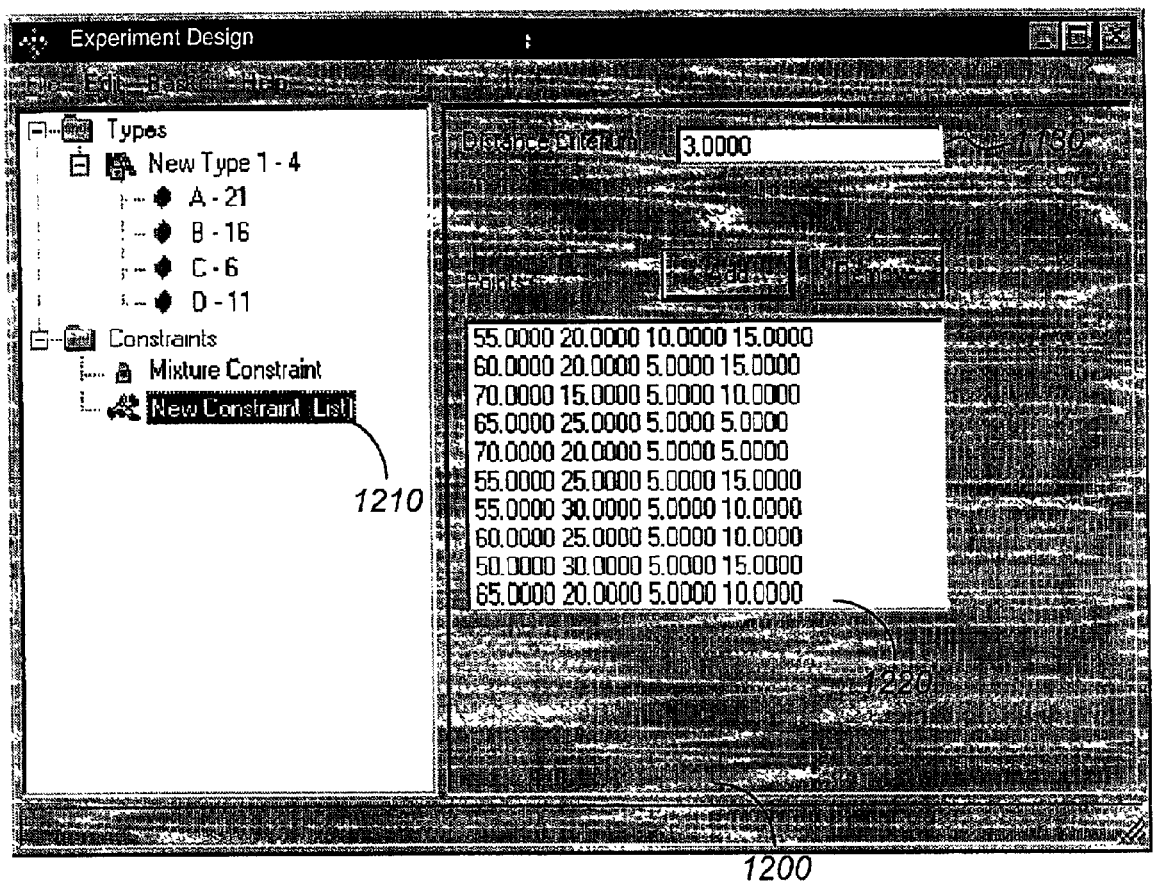
FIG. 12 illustrates an embodiment of a design interface for defining a list constraint on an experiment design.
Figure 13A:
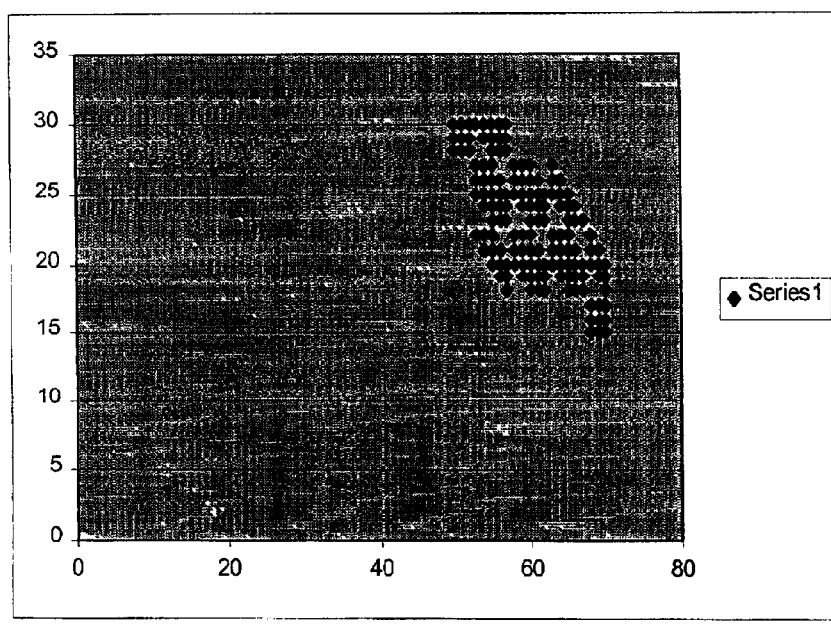
FIGS. 13A–D are a series of graphs illustrating the projection of a set of candidate points in a ABCD parameter space into the AB, AD, CD, and BC planes, respectively.
Figure 13B:
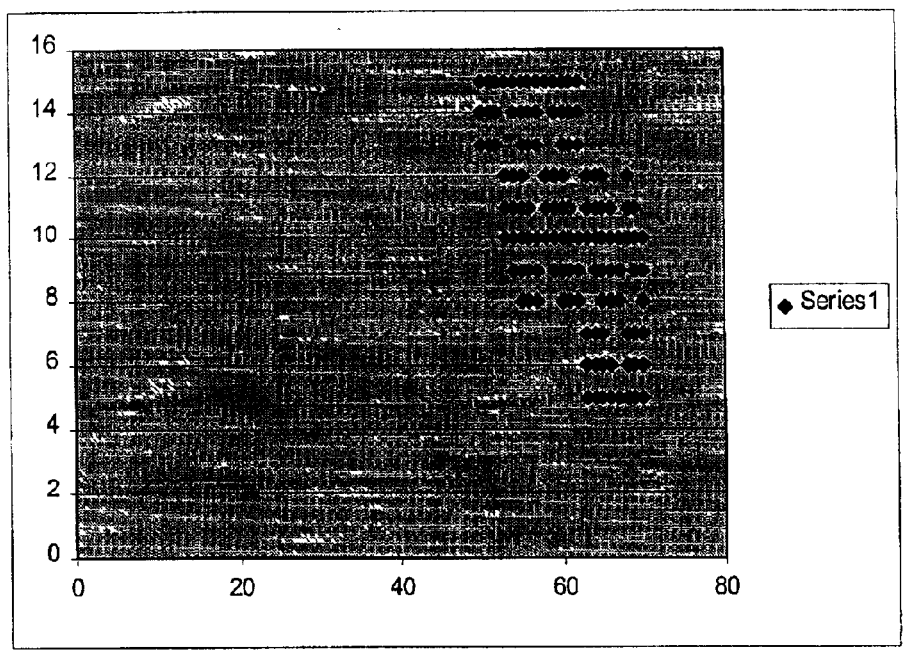
Figure 13C:
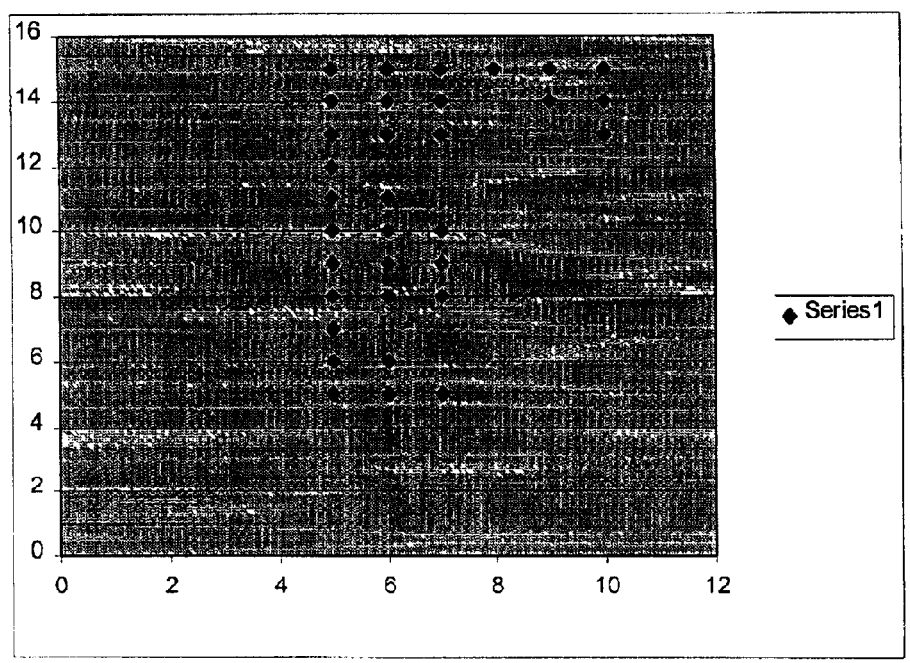
Figure 13D:
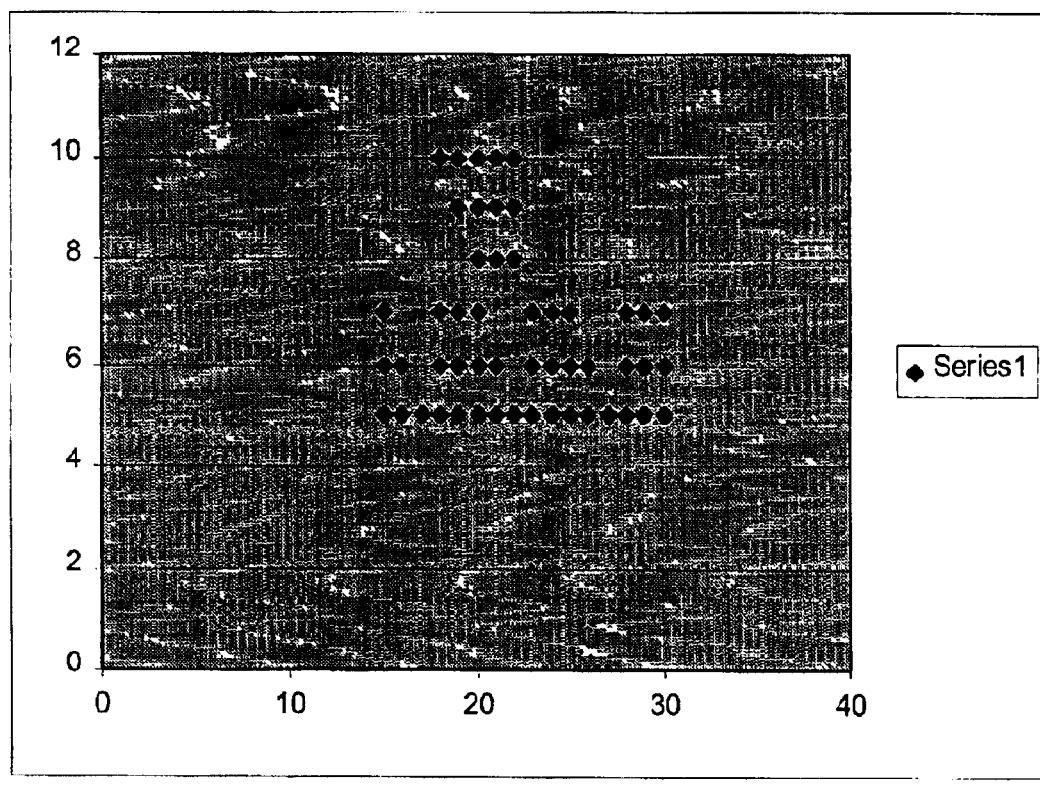

To generate a design focusing on these ten hits, the user generates a new design based on the values observed for these hits, using the notion of proximity between compounds defined as distance between points in the parameter space. First, the user defines the four parameters as described above, specifying a range from 50 to 70% for parameter A, 15 to 30% for parameter B, 5 to 10% for parameter C and 5 to 15% for parameter D, all in steps of 1%. Referring to FIG. 12, the user then defines a list constraint 1210 to enter the list of hits (in field 1220 of workspace 1200), and a distance criterion in field 1230. When the design is complete, design program 130 calculates the expansion in step 360, applying the list constraint for each possible combination of parameters and accepting only the combinations that fall within the specified distance (here 3%) of the points in the parameter space corresponding to hits identified in the list (where distance in the parameter space is expressed according to the formula $$d^2 = \sum_i (X_i - Y_i)^2$$

where $X_i$ are the fractional compositions for compound X and $Y_i$ are the fractional compositions for compound Y). The results are shown in FIGS. 13A–D, each of which represents a different projection of the calculated candidate materials in the ABCD parameter space.

Using design system 100, the scientist populates a parameter space as a volume, rather than as a series of lower-dimensional projections. By applying one or more constraints to the design, the scientist constructs experimental parameter space subsets from the larger "hypothetical" parameter space. Within each experimental parameter space, the scientist can employ various sampling methods to populate the volume. In every case, all manipulations and calculations are performed on volumes, rather than slices or projections of the parameter space.

In an example of traditional, low-dimensional experimentation, the scientist seeks to study the effect of changing composition on electrical conductivity in the binary Ag—Cu system, and needs 1% precision to accurately measure the composition of choice, which is unknown. An initial estimate of sampling precision (based, for example, on the literature, previous calculations or the like) suggests 10% composition steps as reasonable to sample the binary system. The scientist measures electrical conductivity for pure Ag, pure Cu, and mixtures of Ag and Cu in ratios of 1:9, 2:8, 3:7, 4:6, 5:5, 6:4, 7:3, 8:2 and 9:1. Based on initial results, the scientist might carry out more precise follow up experiments between compositions 2:8 and 4:6, with 1% variation, to achieve a satisfactory value for conductivity at a specific composition in this range.

In this example, the problem is conceptually easy. The three dimensions of Ag concentration, Cu concentration and conductivity are reduced to two dimensions by the requirement that the atomic fractions of Ag and Cu must add to 100%. Similarly, the scientist can easily use the desired initial precision (10%) to estimate the total number of initial experiments (11) and follow up experiments (another 18) needed to satisfactorily search the parameter space. Thus, the scientist can quickly determine whether the available resources can synthesize and screen the necessary discrete compositions in an appropriate amount of time.

The limitations of these traditional techniques become apparent when the parameter space is extended to higher dimensions. For example, where the scientist seeks to find the maximum value for a given property in a 10 parameter system (assuming all parameters are independently variable) at a precision of 1%, sampling all compositions would require $3 \times 10^{11}$ experiments. To avoid performing this huge number of experiments, the scientist can adopt a strategy similar to that just described, initially sampling at 10%, followed by a 1% follow up. Sampling a 10 dimensional volume at 10% still requires nearly $10^5$ experiments, however, so the parameter space is traditionally further constrained by sampling projections of reduced dimensionality—for example, starting with binaries and ternaries, then moving to quaternaries, quinaries if possible, and so on. Using the behavior of these low-dimensionality projections, the scientist then typically infers the response at higher dimensionality.

Using the techniques of design system 100, however, the scientist can quickly examine the effect of different constraints and population methods on the experimental parameter space without reducing the dimensionality of the proposed experiments. These changes can be simple—for example, changing the initial sampling precision from 10% to 12%, which reduces the number of points by nearly an order of magnitude—or complicated, such as adopting non-linear sampling methods. The experimental parameter space can be reduced to a manageable size without sacrificing dimensionality, always treating the parameter space as a volume.

Thus, for example, the scientist uses design system 100 to design a set of experiments to search for magnetic compositions made up of combinations of six component materials—three transition metals (A, B and C), two metalloids (D and E) and a rare earth (F). Based on previous experiments, the scientist knows that small changes in composition can have large effects on magnetic properties of the resulting composition, and that many of the lower-order (i.e., ternary) combinations have been studied in previous experiments. Finally, the scientist recognizes that cost, personnel and equipment availability limit the search to 5000 points in the parameter space.

Based on this information, the scientist defines six parameters grouped in three types (TM, M and RE, corresponding to transition metals, metalloids and rare earth, respectively). Because of the known sensitivity of the parameter space to changes in composition, the scientist sets each parameter to vary with a step size of 5%.

Based on these conditions, design program 130 calculates that the scientist's search criteria will require searching 53,130 points, far exceeding the budget of just 5,000 points. The scientist returns to the drawing board to revise the search criteria, reducing the precision by changing the step sizes to 10%. With this one change, design program 130 calculates that just 3,000 points will be required; however, given the known fine precision of the parameter space and the 5,000 point budget, the scientist decides that these criteria result in too coarse a search of the parameter space.

Next, the scientist returns to the original specified precision, returning to step sizes of 5%, but defines a sum constraint to set the total fractional composition of the transition metal materials to greater than 50% of the total composition. These changes, though, push the number of points returned by design program 130 to 28,700, still exceeding the scientist's budget.

To compensate, the scientist revisits the step size, this time changing the specified step size to 10%, but only for the transition metals. Under these conditions—[TM]>50%, (each TM can vary from 0 to 100, but together they must be >50%), TM precision of 10%, metalloid and rare earth precision of 5%, design program 130 calculates a point set of 4,725 coming close to the budget for the project.

The capacity to deal with the parameter space as a volume allows the scientist to implement a variety of well known methods to populate the experimental parameter space.

Design of Experiments, statistical methods, sampling strategies (e.g., random, biased, Monte Carlo), data mining, and feedback from previously-completed experiments can be employed where appropriate to the study in question. By implementing these known techniques in a manner that preserves the volumetric nature of the parameter space, the techniques of design system 100 permit the design of efficient combinatorial experiments without sacrificing the dimensionality of the parameter space.

Using the techniques described herein, system 100 enables users to design a combinatorial program of experiments for complex parameter spaces—for example, spaces defined by four or six parameters, or more preferably ten, fifty or more parameters. Applying any specified constraints, system 100 executes a combinatorial expansion, generating a set of experiments implementing the combinatorial program. In some preferred implementations, the resulting sets of experiments may include 48 or 96 or more different parameter space points, more preferably about 1,000 or 10,000 or more points, and even more preferably about 50,000 or 100,000 or more parameter space points.

Figure 14:
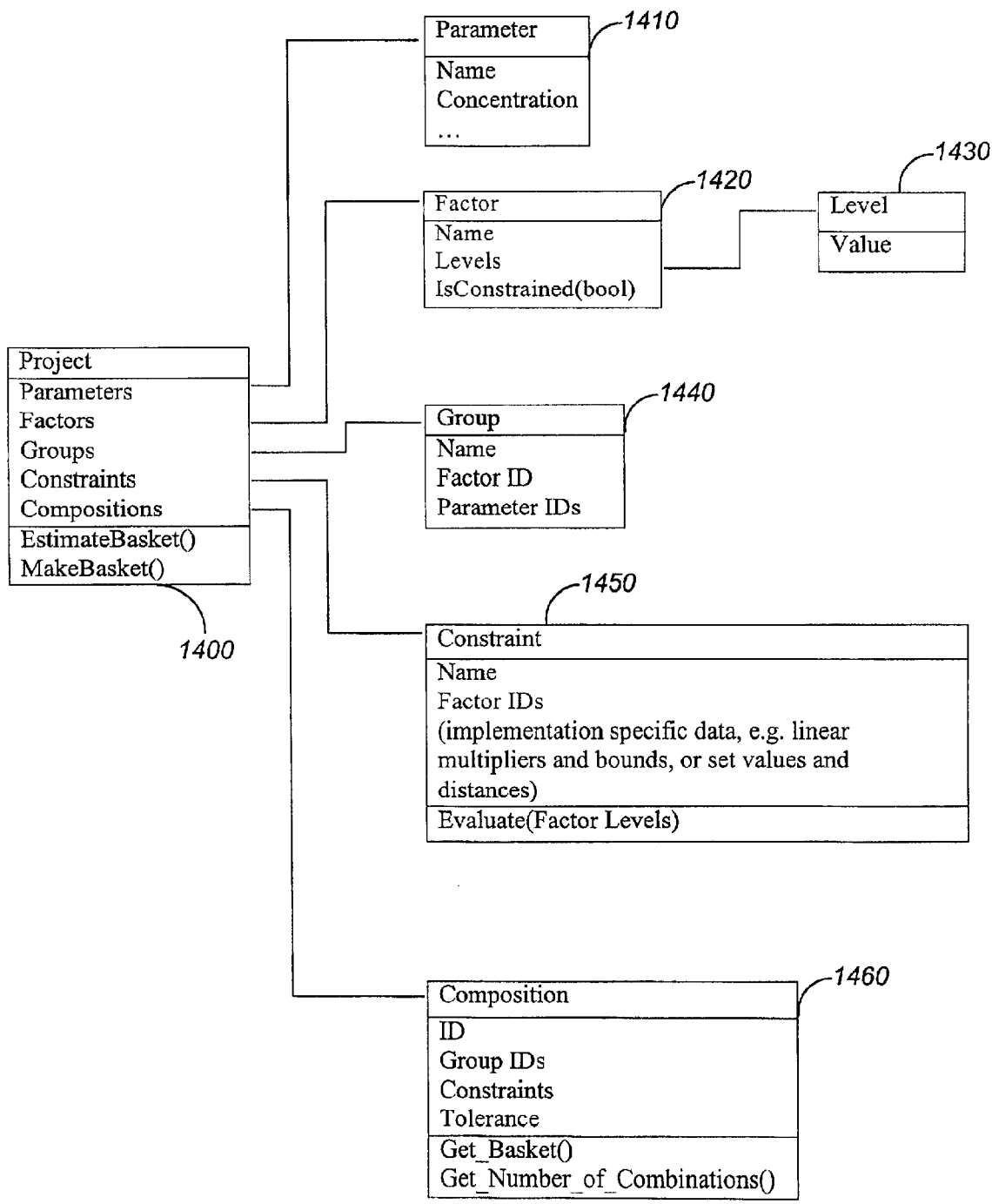
FIG. 14 illustrates an object model suitable for implementation in a combinatorial experiment design program.

In one embodiment, design program 130 can implement an object model as illustrated in FIG. 14, using known object-oriented programming techniques. Project object 1400 is a top-level object representing a set of combinatorial experiments. For each set of experiments, the corresponding Project object has a set of properties including Parameters, Factors, Groups, Compositions and Constraints object collections, each of which will be discussed in more detail below. The Project object also captures meta information about the user responsible for generating the experiment design, the date, and the like. The Project object's methods include an EstimateBasket function, which takes as inputs values for each of the Project object's properties and returns the size of the combinatorial expansion defined by those property values. Similarly, the MakeBasket function is responsible for actually generating the combinatorial expansion by iterating over the individual compositions in the expansion, which will be discussed in more detail below.

Parameter objects 1410 represent the parameters to be used in the library design. As discussed above, these can include process parameters and physical parameters, such as process conditions, physical characteristics or component materials (e.g., temperature, pressure, annealing time, molecular weight, grain size, or the identity of particular elements, compounds or compositions, which may themselves include one or more elements or compounds, in a gaseous, liquid or solid phase). Properties include a name (ID) and information related to the Parameter's properties (e.g., for a component material, chemical composition properties, such as the name of one or more elements, mixtures or chemicals that make up the material, molecular weight, equivalents, structure, density, concentration, or the like).

Factor objects 1420 express how a particular parameter enters a composition. In this context, a composition represents the contribution of a particular parameter to each experiment in a Project. Properties include a name (ID), one or more Levels objects, which identify the allowed levels for the corresponding parameter, and a Boolean object identifying whether the parameter associated with the Factor object is considered to be constrained as part of a mixture, or if it is unconstrained and requires a full factorial expansion.

As described above, Level objects 1430 identify allowed Factor object values. A Level object's Value property can take any numeric or string value where the parameter associated with the corresponding Factor object is unconstrained, and can take values between 0% and 100% for constrained parameters. For example:

Factor object: Stir; Levels: On, Off.
Factor object: Temperature; Levels (° C.): 100, 110, 120.
Factor object: Catalyst; Levels (%): 0, 10, 20, 30, 40, 55, 85.

Group objects 1440 associate one or more parameters with a specific Factor object. The Group object's properties include a name (ID), a Factor ID and one or more Parameter IDs. The effect is to provide that the parameters corresponding to the specified Parameter IDs will be present in the ultimate composition according to the levels set in the Factor object having the specified Factor ID. For example, Group: TM (Transition Metals); Factor object: Catalyst; Parameters: Fe, Ni, Cd denotes a Group object having the name TM (representing transition metals to be incorporated in a composition) and providing that the Fe, Ni and Cd Parameters (component materials) will be included in the overall composition at levels set in the Catalyst Factor object.

Constraint object 1450 has properties that include a name (ID), a list of Factors IDs and a set of mathematical conditions. The EvaluateFactor function takes as input the values for the specified Factor objects and applies the specified conditions, returning true or false depending on the type of conditions. For example, in one implementation, the constraint can be represented mathematically as a linear combination of factors (having numerical values) and either an upper or a lower limit or both. The constraint evaluates to true if the mathematical value of the linear combination of Factor object levels falls within the limits. In another implementation, the constraint can be represented by a single set of levels for each Factor object and a distance criterion for each of them. In this case the constraint evaluates to true if each Factor object level falls within (or outside of) the given distance from the set value. In another implementation the constraint expresses a fixed ratio between two or more Factor objects, and it evaluates to true if the Factor object levels satisfy the numerical relationship. For Factor objects having non-numerical levels, constraints can specify a Boolean relationship, such as, e.g., "stir AND heat".

Composition object 1460 expresses how a set of groups is combined to form an experiment design. Properties include name (ID) and a set of Group IDs, which represent a combination of one parameter from each group according to the levels expressed by each group Factor object. The Composition object can also include one or more Constraints properties listing a set of constraints that apply to the specific combination of groups. Finally, a tolerance value can be provided. For example, a Composition object ABC having Group properties corresponding to three groups A, B, and C as follows:

Group A: Factor object 1, Parameters x, y, z;
Group B: Factor object 2, Parameters w, t;
Group C: Factor object 3, Parameters s, r; can define a composition 1 of ABC having a total of 3×2×2=12 combinations. These combinations represent the set of all ternary combinations that can be constructed with the specified parameters where parameters in the same group cannot be combined (e.g., xws, xwr, yts, zws, etc). A Composition object can specify combinations including more than one member of a given group (e.g., where the Group ID for a group is repeated twice in the Composition object properties). Thus, a composition AAB having the same Group properties as the ABC group discussed above can define a total of 3×2=6 combinations (where duplications are excluded), representing the set of ternaries AAB that can be constructed with the same parameters (e.g., xyw, xzt, yzw, etc).

Note that in these examples, the total number of combinations must be multiplied by the number of combinations allowed by the full factorial expansion of the groups' factors. Therefore each combination represents a whole ternary of experiments. These examples include only the ternary combinations—i.e., not binaries such as AA and AB binaries, which would be provided by adding Composition objects of the form, e.g., AA or AB, to the project. The Composition object's Get_Number_of_Combinations( ) function returns the number of possible combinations of the composition. If the group names are all distinct, this corresponds to the product of the number of parameters in each group. If a group name is repeated, then the binomial formula must be used for that subgroup. The Get_Basket( ) function returns the portion of the experiment design associated with that specific composition (i.e., the contribution of the specified Composition object to each experimental point in the combinatorial expansion).

In one implementation, the Get_Basket( ) function operates as follows. The function first calculates the template basket from the Factor objects of each group, essentially building a set of nested loops over each Factor object level. This can be analogized, for example, to a car odometer, where each Factor object corresponds to one decimal place in the odometer, and each Factor object level a digit in the corresponding place. The odometer is initialized to the first level of all Factor objects. The rightmost place spins fastest, going through each of the Factor object level in order. After a complete revolution of the rightmost place, the place to its immediate left is given its next level, and so on. For each "mileage", each of the constraints listed in the compositions is evaluated, and the combination of levels is added to the basket if and only if all constraints evaluate to "true". There is an implicit constraint for "constrained" Factor objects—that the sum of the relative concentrations of each component material must be 100% plus or minus the specified tolerance value. The calculation can be optimized based on the particular constraints defined for the composition. Thus, in one implementation, the time required to scan the possible configurations can be reduced by evaluating the effect of the constraints on the maximum and minimum allowed level values. For example, for a composition based on two factors constrained to take values between 10 and 90, with a global constraint that the sum be 100, the value for the second level can be derived from the value of the first level and the global constraint, decreasing the necessary computation time. In general, the size of the required computation can be determined by heuristically determining the set of conditions on the Factor object levels imposed by the set of constraints.

After the template basket has been composed, a similar "odometer" is built out of the groups' parameters, provided that, if a group is repeated, a parameter cannot appear more than once on the "odometer". For each "mileage" on the odometer, the template basket is added to the composition basket with factors replaced by parameters. The total "basket", representing the portion of the combinatorial expansion for the particular groups, is returned to the function caller (which may be, for example, the MakeBasket function of a Project object, which iterates over the baskets for each Composition object in the project to generate a total experimental basket).

The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with users. In a preferred implementation, the graphical user interface can include a "Design Wizard" providing a series of help dialogs for assisting users in the performance of the functions of the invention.

A number of implementations of the invention have been described. Nevertheless, it will be understood that various modifications may be made without departing from the spirit and scope of the invention. Accordingly, other embodiments are within the scope of the following claims.

What is claimed is:

1. A computer program product on a computer-readable medium for designing a set of experiments, the program comprising instructions operable to cause a programmable processor to:

receive input defining a set of experimental parameters, one or more sampling patterns defining a sampling for each parameter of the set of experimental parameters, and one or more constraints limiting the set of experiments to a particular volume or volumes of a hyperspace defined by the set of experimental parameters, at least a plurality of the set of parameters being grouped according to a parameter type such that the grouped parameters are constrained to perform a common role in the set of experiments;

generate a first estimate of the practicability of a first set of experiments defined by the parameters, the sampling patterns and the constraints, the first estimate including a count of the set of experiments defined by the set of experimental parameters, the sampling patterns and the constraints, and provide the first estimate to a user;

receive input modifying at least one of the set of parameters, the sampling patterns or the constraints in response to the first estimate;

in response to the input modifying at least one of the set of parameters, the sampling patterns or the constraints, generate a second estimate of the practicability of a second set of experiments defined by the set of experimental parameters defined by the parameters, the sampling patterns and the constraints, including the modified parameters, sampling patterns or constraints, the second estimate including a count of the second set of experiments, and provide the second estimate to the user, and in response to input approving of the second estimate, generate an experiment design defined by the parameters, the sampling patterns and the constraints, the experiment design including data representing a final set of experiments, the data including a plurality of sets of coordinates in the hyperspace defined by the set of experimental parameters, each of the sets of coordinates defining an experiment in the final set of experiments.

2. The computer program product of claim 1, wherein: the sampling patterns include at least a first sampling pattern defined for a first parameter of the set of experimental parameters and a second sampling pattern defined for a second parameter of the set of experimental parameters, wherein the first sampling pattern is different from the second sampling pattern.

3. The computer program product of claim 2, wherein: at least one of the first and second sampling patterns includes a gradient of parameter values defined by a minimum parameter value, a maximum parameter value and a step size.

4. The computer program product of claim 3, wherein: the first and second sampling patterns are defined by first and second gradients.

5. The computer program product of claim 1, wherein: the set of experimental parameters includes a plurality of component materials to be used in the set of experiments.

6. The computer program product of claim 5, wherein: the set of experimental parameters includes at least one process condition to be varied in the set of experiments.

7. The computer program product of claim 5, wherein: the constraints include a mixture constraint limiting the fractional contribution of at least a plurality of the component materials to a total composition in one or more of the experiments in the set of experiments.

8. The computer program product of claim 7, wherein: the mixture constraint specifies a minimum number of component materials to be included in one or more of the experiments in the set of experiments.

9. The computer program product of claim 8, wherein: the mixture constraint specifies a maximum number of component materials to be included in one or more of the experiments in the set of experiments.

10. The computer program product of claim 5, wherein: the constraints include a type constraint limiting the total number of parameters of a specified type to be included in one or more of the experiments in the set of experiments.

11. The computer program product of claim 5, wherein: the constraints include a sum constraint limiting the sum of a contribution of parameters of a specified type to one or more of the experiments in the set of experiments.

12. The computer program of claim 5, wherein: the constraints include a balance constraint limiting the contribution of at least one parameter to a plurality of experiments of the set of experiments based on the contribution of one or more other parameters to one or more of the experiments in the set of experiments.

13. The computer program product of claim 5, wherein: the constraints include a list constraint identifying a list of one or more starting compositions to be used to generate the set of experiments.

14. The computer program product of claim 13, wherein: each of the starting compositions is represented as a point in the hyperspace defined by the set of experimental parameters; and the list constraint specifies a distance criterion specifying an acceptable distance in the hyperspace from the points corresponding to the starting compositions.

15. The computer program product of claim 13, wherein: the one or more starting compositions are derived from results of a previous experiment.

16. The computer program product of claim 5, wherein: the constraints include a synthesis constraint specifying an order in which a plurality of component materials are to be added in a synthesis to be performed in one or more of the experiments in the set of experiments.

17. The computer program product of claim 16, wherein: the synthesis constraint specifies that the order in which component materials are to be added is to vary between a plurality of experiments in the set of experiments.

18. The computer program product of claim 5, wherein:
the constraints include a process constraint specifying an order in which a plurality of process steps are to be performed in one or more of the experiments in the set of experiments.

19. The computer program product of claim 18, wherein:
the process constraint specifies that the order in which process steps are to be performed is to vary between a plurality of experiments in the set of experiments.

20. The computer program product of claim 1, wherein:
the constraints include a project constraint specifying the order in which individual experiments in the set of experiments are to be performed.

21. The computer program product of claim 20, wherein:
the project constraint includes a priority value assigned to one or more of the set of experiment parameters, the priority value representing a relative priority attached to the corresponding parameter.

22. The computer program product of claim 5, wherein:
the constraints include one or more chemistry-specific constraints selected from balance constraints, electron-counting constraints, atomic size constraints, ionic size constraints, atomic packing constraints, ionic packing constraints, heat of formation constraints, or entropy constraints.

23. The computer program product of claim 1, wherein:
at least one of the constraints includes one or more tolerance values representing an amount by which the corresponding constraint can be relaxed during generation of the experiment design.

24. The computer program product of claim 1, wherein the instructions operable to generate the experiment design include instructions operable to cause a programmable processor to:
identify a plurality of points in the hyperspace defined by the set of experimental parameters corresponding to candidate materials by counting through parameter space points defined by the sampling pattern and applying the experimental constraints to the parameter space points.

25. The computer program product of claim 1, wherein:
the set of experimental parameters includes at least four experimental parameters.

26. The computer program product of claim 1, wherein:
the set of experimental parameters includes at least six experimental parameters.

27. The computer program product of claim 1, wherein:
the set of experimental parameters includes at least ten experimental parameters.

28. The computer program product of claim 1, wherein:
the set of experimental parameters includes at least fifty experimental parameters.

29. The computer program product of claim 1, wherein:
the final set of experiments includes at least 48 experiments.

30. The computer program product of claim 1, wherein:
the final set of experiments includes at least 96 experiments.

31. The computer program product of claim 1, wherein:
the final set of experiments includes at least 1,000 experiments.

32. The computer program product of claim 1, wherein:
the final set of experiments includes at least 10,000 experiments.

33. The computer program product of claim 1, wherein:
the final set of experiments includes at least 50,000 experiments.

34. The computer program product of claim 1, wherein:
the final set of experiments includes at least 100,000 experiments.

35. The computer program product of claim 5, wherein:
each of the component materials has an associated set of material properties describing the component material; and
the instructions operable to cause a programmable processor to receive input defining the set of experimental parameters include instructions operable to cause a programmable processor to receive for each of the component materials a set of values for one or more of the material properties associated with the component material.

36. The computer program product of claim 35, wherein:
at least one of the material properties is selected from the group consisting of molecular weight, equivalents, density and concentration.

37. The computer program product of claim 35, wherein:
at least one of the material properties is a type describing a class of chemicals to be used in generating the experiment design.

38. A computer-implemented method for designing a set of experiments, comprising:
receiving input defining a set of experimental parameters, one or more sampling pattern defining a sampling for each parameter of the set of experimental parameters, and one or more constraints limiting the set of experiments to a particular volume or volumes of a hyperspace defined by the set of experimental parameters, at least a plurality of the set of parameters being grouped according to a parameter type such that the grouped parameters are constrained to perform a common role in the set of experiments;

generating a first estimate of the practicability of a first set of experiments defined by the parameters, the sampling patterns and the constraints, the first estimate including a count of the set of experiments defined by the set of experimental parameters, the sampling patterns and the constraints, and providing the first estimate to a user;

receiving input modifying at least one of the set of parameters, the sampling patterns or the constraints in response to the first estimate;

in response to the input modifying at least one of the set of parameters, the sampling patterns or the constraints, generating a second estimate of the practicability of a second set of experiments defined by the parameters, the sampling patterns and the constraints, including the modified parameters, sampling patterns or constraints, the second estimate including a count of the second set of experiments, and providing the second estimate to the user; and in response to input approving of the second estimate, generating an experiment design defined by the parameters, the sampling patterns and the constraints, the experiment design including data representing a final set of experiments, the data including a plurality of sets of coordinates in the hyperspace defined by the set of experimental parameters, each of the sets of coordinates defining an experiment in the final set of experiments.

39. The method of claim 38, further comprising:
using the experiment design to synthesize one or more combinatorial libraries including a plurality of compositions defined by the coordinates of the experiment design.

40. The method of claim 38, wherein:
the sampling patterns include at least a first sampling pattern defined for a first parameter of the set of experimental parameters and a second sampling pattern defined for a second parameter of the set of experimental parameters, wherein the first sampling pattern is different from the second sampling pattern.

41. The method of claim 38, wherein:
the set of experimental parameters includes a plurality of component materials to be used in the set of experiments.

42. The method of claim 41, wherein:
the set of experimental parameters includes at least one process condition to be varied in the set of experiments.

43. The method of claim 41, wherein:
the constraints include a mixture constraint limiting the fractional contribution of at least a plurality of the component materials to a total composition in one or more of the experiments in the set of experiments.

44. The method of claim 41, wherein:
the constraints include a type constraint limiting the total number of parameters of a specified type to be included in one or more of the experiments in the set of experiments.

45. The method of claim 41, wherein:
the constraints include a sun constraint limiting the sum of a contribution of parameters of a specified type to one or more of the experiments in the set of experiments.

46. The method of claim 41, wherein:
the constraints include a balance constraint limiting the contribution of at least one parameter to a plurality of experiments of the set of experiments based on the contribution of one or more other parameters to one or more of the experiments in the set of experiments.

47. The method of claim 41, wherein:
the constraints include a list constraint identifying a list of one or more starting compositions to be used to generate the set of experiments.

48. The method of claim 41, wherein:
the constraints include a synthesis constraint specifying an order in which a plurality of component materials are to be added in a synthesis to be performed in one or more of the experiments in the set of experiments.

49. The method of claim 48, wherein:
the synthesis constraint specifies that the order in which component materials are to be added is to vary between a plurality of experiments in the set of experiments.

50. The method of claim 41, wherein;
the constraints include a process constraint specifying an order in which a plurality of process steps are to be performed in one or more of the experiments in the set of experiments.

51. The method of claim 50, wherein:
the process constraint specifies that the order in which process steps are to be performed is to vary between a plurality of experiments in the set of experiments.

52. The method of claim 41, wherein:
each of the component materials has an associated set of material properties describing the component material; and
receiving input defining the set of experimental parameters includes receiving for each of the component materials a set of values for one or more of the material properties associated with the component material.

53. The method of claim 52, wherein:
at least one of the material properties is selected from the group consisting of molecular weight, equivalents, density and concentration.

54. The method of claim 52, wherein:
at least one of the material properties is a type describing a class of chemicals to be used in generating the experiment design.

55. The method of claim 38, wherein:
the constraints include a project constraint specifying the order in which individual experiments in the set of experiments are to be performed.

56. The method of claim 38, wherein:
at least one of the constraints includes one or more tolerance values representing an amount by which the corresponding constraint can be relaxed during generation of the experiment design.

57. The method of claim 38, wherein:
generating the experiment design includes identifying a plurality of points in the hyperspace defined by the set of experimental parameters corresponding to candidate materials by counting through parameter space points defined by the sampling pattern and applying the experimental constraints to the parameter space points.

58. The method of claim 38, wherein:
the set of experimental parameters includes at least four experimental parameters.

59. The method of claim 38, wherein:
the set of experimental parameters includes at least six experimental parameters.

60. The method of claim 38, wherein:
the set of experimental parameters includes at least ten experimental parameters.

61. The method of claim 38, wherein:
the set of experimental parameters includes at least fifty experimental parameters.

62. The method of claim 38, wherein:
the final set of experiments includes at least 48 experiments.

63. The method of claim 38, wherein:
the final set of experiments includes at least 96 experiments.

64. The method of claim 38, wherein:
the final set of experiments includes at least 1,000 experiments.

65. The method of claim 38, wherein:
the final set of experiments includes at least 10,000 experiments.

66. The method of claim 38, wherein:
the final set of experiments includes at least 50,000 experiments.

67. The method of claim 38, wherein:
the final set of experiments includes at least 100,000 experiments.

68. A computer-implemented experiment design system, comprising:
means for defining a set of experimental parameters, one or more sampling patterns defining a sampling for each parameter of the set of experimental parameters, and one or more constraints limiting the set of experiments to a particular volume or volumes of a hyperspace defined by the set of experimental parameters, at least a plurality of the set of parameters being grouped according to a parameter type such that the grouped parameters are constrained to perform a common role in the set of experiments;

means for generating an estimate of the practicability of a set of experiments defined by the parameters, the sampling patterns and the constraints, the estimate including a count of the set of experiments defined by the set of experimental parameters, the sampling patterns and the constraints;

means for generating, in response to a user input approving of the estimate, an experiment design defined by the parameters, the sampling patterns and the constraints, the experiment design including data representing a final set of experiments, the data including a plurality of sets of coordinates in the hyperspace defined by the set of experimental parameters, each of the sets of coordinates defining an experiment in the final set of experiments.

69. The experiment design system of claim 68, further comprising:

means for synthesizing based on the experiment design one or more combinatorial libraries including a plurality of compositions defined by the coordinates of the experiment design.

70. The experiment design system of claim 69, wherein: the set of experimental parameters includes at least ten experimental parameters.

71. The experiment design system of claim 69, wherein: the final set of experiments includes at least 1,000 experiments.

72. A computer program product on a computer-readable medium for designing a set of experiments, the program comprising instructions operable to cause a programmable processor to:

receive input defining a set of experimental parameters, one or more sampling patterns defining a sampling of each parameter of the set of experimental parameters, and one or more constraints limiting the set of experiments to a particular volume or volumes of a hyperspace defined by the set of experimental parameters, at least a plurality of the set of parameters being mixture parameters defining a plurality of component materials to be used in the set of experiments to generate a mixture, the sampling patterns defined for the mixture parameters defining a non-uniform sampling of the mixture parameters; and generate an experiment design defined by the parameters, the sampling patterns and the constraints, the experiment design including data representing a final set of experiments, the data including a plurality of sets of coordinates in the hyperspace defined by the set of experimental parameters, each of the sets of coordinates defining an experiment in the final set of experiments.

73. A computer program product on a computer-readable medium for designing a set of experiments, the program comprising instructions operable to cause a programmable processor to:

receive input defining a set of experimental parameters, one or more sampling patterns defining a sampling of each parameter of the set of experimental parameters, and one or more constraints limiting the set of experiments to a particular volume or volumes of a hyperspace defined by the set of experimental parameters, at least a plurality of the set of parameters being mixture parameters defining a plurality of component materials to be used in the set of experiments to generate a mixture, the constraints including a mixture constraint limiting the fractional contribution of at least a plurality of the component materials to a total composition in one or more of the experiments in the set of experiments, the mixture constraint including one or more tolerance values representing an amount by which the mixture constraint can be relaxed during generation of an experiment design; and generate an experiment design defined by the parameters, the sampling patterns and the constraints, the experiment design including data representing a final set of experiments, the data including a plurality of sets of coordinates in the hyperspace defined by the set of experimental parameters, each of the sets of coordinates defining an experiment in the final set of experiments.

74. A computer program product on a computer-readable medium for designing a set of experiments, the program comprising instructions operable to cause a programmable processor to:

receive input defining a set of experimental parameters, one or more sampling patterns defining a sampling of each parameter of the set of experimental parameters, and one or more constraints limiting the set of experiments to a particular volume or volumes of a hyperspace defined by the set of experimental parameters, at least a plurality of the set of parameters being mixture parameters defining a plurality of component materials to be used in the set of experiments to generate a mixture, the constraints including a balance constraint limiting the contribution of at least one of the mixture parameters to the experiment design based on the contribution of a plurality of other mixture parameters to one or more of the experiments in the set of experiments; and generate an experiment design defined by the parameters, the sampling patterns and the constraints, the experiment design including data representing a final set of experiments, the data including a plurality of sets of coordinates in the hyperspace defined by the set of experimental parameters, each of the sets of coordinates defining an experiment in the final set of experiments.

* * * * *

UNITED STATES PATENT AND TRADEMARK OFFICE
CERTIFICATE OF CORRECTION

PATENT NO. : 6,983,233 B1
DATED : January 3, 2006
INVENTOR(S) : Falcioni et al.

It is certified that error appears in the above-identified patent and that said Letters Patent is hereby corrected as shown below:

Title page,
Item [56], References Cited, U.S PATENT DOCUMENTS, add the following:
-- 4,368,509 A    1/1983      Li                  364/148
   4,472,770 A    9/1984      Li                  364/148
   4,710,864 A    12/1987     Li                  364/148
   6,411,945 A    6/2002      Nakajima            706/19
   6,618,852 A    9/2003      Van Eikeren et al.  717/108 --.
OTHER PUBLICATIONS, add the following:
-- Kagaku, "Combinatorial Chemistry: Inconceivable without Computers", *Combinatorial Chemistry*, Vol. 51, No. 8, pp. 480-483 and 583 (1996).
Yamagata et al., "Constructing an Assay System with HTS", *IV High Throughput Screening*, pp. 179-191 (1997). --.
"Maier" reference, should read -- "Combinatorial Chemistry—Challenge and Chance for the Development of New Catalysts and Materials," Agnew. Chem. Int. Ed., 1999, 38, 1216. --;

Signed and Sealed this

Fourth Day of April, 2006

JON W. DUDAS
*Director of the United States Patent and Trademark Office*